United States Patent
Myc et al.

(10) Patent No.: US 12,194,085 B2
(45) Date of Patent: Jan. 14, 2025

(54) VACCINE FOR THE PREVENTION AND TREATMENT OF C. DIFFICILE INFECTIONS AND THE USE THEREOF

(71) Applicant: Instytut Immunologii I Terapii Doswiadczalnej Im. Ludwika Hirszfelda Polskiej Akademii Nauk, Wroclaw (PL)

(72) Inventors: Andrzej Myc, Wroclaw (PL); Agnieszka Razim, Zabrze (PL); Sabina Gorska, Wroclaw (PL); Andrzej Gamian, Wroclaw (PL)

(73) Assignee: INSTYTUT IMMUNOLOGii I TERAPii DOSWiADCZALNEJ LM. LUDWiKA HiRSZFELDA POLSKiEJ AKADEMii NAUK, Wroclaw (PL)

( * ) Notice: Subject to any disclaimer, the term of this patent is extended or adjusted under 35 U.S.C. 154(b) by 895 days.

(21) Appl. No.: 17/299,268

(22) PCT Filed: Dec. 3, 2019

(86) PCT No.: PCT/IB2019/060389
§ 371 (c)(1),
(2) Date: Jun. 2, 2021

(87) PCT Pub. No.: WO2020/115648
PCT Pub. Date: Jun. 11, 2020

(65) Prior Publication Data
US 2022/0031826 A1 Feb. 3, 2022

(30) Foreign Application Priority Data
Dec. 4, 2018 (PL) .......................... 428045

(51) Int. Cl.
*A61K 39/08* (2006.01)
*A61K 39/39* (2006.01)
*A61K 39/00* (2006.01)

(52) U.S. Cl.
CPC ............. *A61K 39/08* (2013.01); *A61K 39/39* (2013.01); *A61K 2039/541* (2013.01); *A61K 2039/55505* (2013.01); *A61K 2039/55555* (2013.01)

(58) Field of Classification Search
None
See application file for complete search history.

(56) References Cited

FOREIGN PATENT DOCUMENTS

WO   WO 2009/131995 A1   10/2009
WO   WO 2010/036938 A2   4/2010

OTHER PUBLICATIONS

Pamela T. Wong et al: "Formulation, High Throughput In Vitro Screening and In Vivo Functional Characterization of Nanoemulsion-Based Intranasal Vaccine Adjuvants", PLOS ONE vol. 10, No. 5, May 11, 2015 (May 11, 2015), p. e0126120, XP055514988.
De Bruyn Guy et al: "Defining the optimal formulation and schedule of a candidate toxoid vaccine against Clostridium difficile infection: a randomized Phase 2 clinical trial", Vaccine, Elsevier, Amsterdam, NL. vol. 34, No. 19, Mar. 21, 2016 (Mar. 21, 2016), pp. 2170-2178.
Bruxelle J-F et al: "Immunogenic properties of the surface layer precursor of Clostridium difficile and vaccination assays in animal models", Anaerobe, London, GB, vol. 37, Oct. 24, 2015 (Oct. 24, 2015), pp. 78-84, XP029410094.
Severine Pechine et al: Targeting Clostridium difficile Surface Components to Develop Immunotherapeutic Strategies Against Clostridium difficile Infection, Frontiers in Microbiology, vol. 9 May 23, 2018 (May 23, 2018), 11 pages XP055610267.
Razim et al: "Mapping Epitopes of a Novel Peptidoglycan Cross-Linking Enzyme Cwp22 Recognized by Human Sera Obtained from Patients with Clostridioides difficile Infection and Cord Blood", Microorganisms, vol. 7. No. 11, 18 pages, 2019.
International Search Report Mar. 2, 2020 5 pages.

*Primary Examiner* — Oluwatosin A Ogunbiyi
(74) *Attorney, Agent, or Firm* — Ralph E. Jocke; WALKER & JOCKE

(57) ABSTRACT

The present invention relates to a veterinary vaccine containing nanoadjuvants in the form of emulsion and *Clostridium difficile* antigens, as well as the use of the vaccine in the preventions and treatment of a *C. difficile* infection, especially in birds and mammals. The object of the invention is also the use of this vaccine to produce *C. difficile*-specific antibodies.

19 Claims, 10 Drawing Sheets
Specification includes a Sequence Listing.

VACCINE FOR THE PREVENTION AND TREATMENT OF C. DIFFICILE INFECTIONS AND THE USE THEREOF

CROSS-REFERENCE TO RELATED APPLICATIONS

This application is the National Stage entry of International Application No. PCT/IB2019/060389, filed Dec. 3, 2019, which claims priority to Poland Patent Application No. P.428045, filed Dec. 4, 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03 (a)), a Sequence Listing in the form of an ASCII-compliant text file (entitled "Sequence_Listing_3000057-003000_ST25.txt" created on, and 20,141 bytes in size) is submitted concurrently with the instant application, and the entire contents of the Sequence Listing are incorporated herein by reference.

BACKGROUND

Field

The present invention relates to a veterinary vaccine comprising nanoadjuvants in the form of emulsions and *Clostridium difficile* antigens, as well as the use of the vaccine for the prevention and treatment of *C. difficile* infections, especially in birds and mammals.

Description of Related Art

For many years, until its discovery in 1935, *C. difficile* (CD) was considered a non-pathogenic microorganism of the natural microbiota of humans, farm animals and pets. In the 21st century, the probability of being exposed to *C. difficile* spores through the environment and food contaminated with faeces of infected animals is a huge problem. Furthermore, apart from considerations on its zoonotic spread, *C. difficile* is also an expensive disease of animals and animal production. In Europe, veterinary services, even those concerning only the treatment of severe diarrhoea without further complications, generate very high costs. For farm animals, the damage caused by *C. difficile* and the cost of treatment has not yet been established but *C. difficile* can cause mortality in animal husbandry, weight loss and delayed weight gain of the infected subjects (Rodriguez-Palacios et al. 2013; Squire and Riley 2013).

A wide range of zoonoses can be transmitted from poultry to humans. However, only a few studies have been focused on researching the prevalence of *C. difficile* in those animals. Limited available data suggest that the situation is similar to that of other species and the prevalence of infections decreases with age (from 100% in faecal samples of 14-days old birds to 0.29% in adult farm animals) and with bacterial colonisation observable with or without the development of the disease.

Due to the observed problems caused by *C. difficile*, there is a need for efficient methods of preventing infections, which would be safe both for farm animals and humans.

Emulsion-based adjuvants, such as e.g. a nanoemulsion, are known in the art. The nanoemulsion consists of soybean oil, a set of non-ionic and cationic detergents, an organic solvent, and water. The best described nanoemulsion, W805EC, consists of soybean oil, cationic detergent CPC, non-ionic detergent in the form of Tween80, ethanol, and water. Nanoemulsions have been discussed in extensive scientific literature [1-6]. Because of the particle size of approx. 200 nm in diameter and positive potential, nanoemulsion allows for an interaction with many protein antigens. Nanoemulsion particles charged in such a way can interact with the cell membrane of immunocompetent cells, including antigen-presenting cells. Efficient sampling of the nanoemulsion-bound antigen accelerates the processing of the antigen by APC and, consequently, presenting of the antigen to T cells, which initiates a cellular response and then a humoral response created as a result of interactions between T and B cells. In this complicated process, it is important that the process-aiding factor, namely the nanoemulsion, does not contain its own antigens and does not induce an immune response or allergy to the nanoemulsion in the organism. It can occur when traces of protein are present in the nanoemulsion. Formulating nanoemulsions using soybean oil can lead to this situation. Even in its purest form, soybean oil may contain traces of proteins. That is why it is better to replace any vegetable oil with mineral oil or silicone oil, which inherently do not contain any proteins.

Immunoreactive proteins isolated from *Clostridium difficile* strains, such as flagella proteins or S-layer proteins (HMW-SLP, LMW-SLP, Cwp66, Cwp84) [7] are known. Some of them are tested as vaccine components, however, mutants lacking e.g. both SLP proteins (Av-CD 291.2 strain) have already appeared, which means that there is a need to seek new targets on the CD surface.

Various vaccines against diseases caused by *C. difficile* are known in the art. For example, in US20070231336A1 the inventors provided a method of treating *C. difficile* infections (CDI—*Clostridium difficile* infection) in humans. The method includes transdermal administration to a patient (e.g. intramuscularly, intravenously or intraperitoneally) a polyclonal immunoglobulin against *C. difficile*, which neutralises both toxin A and toxin B (e.g. 0.01-100 mg/kg of body mass). Those methods can also include transdermal administration of *Clostridium* toxin or toxoid to a patient in order to stimulate the immune response against *C. difficile* in a patient. When administered to humans affected by the disease, the injected immunoglobulin will also prevent relapses.

U.S. Pat. No. 9,889,196 B2 discloses adjuvant vaccines for the immunisation of birds in ovo. In those vaccines, the adjuvant is in the form of oil-in-water emulsions or microemulsions, the oil being a mineral oil.

Documents describing the use of vaccines composed similarly but directed anti-virally are known in the art, for example, the document US 20130064867 A1 discloses a vaccine composition against the respiratory syncytial virus (RSV) used in the form of nanoemulsion comprising at least one RSV immunogen in combination with an emulsion-based adjuvant. Microemulsion of the RSV vaccine induces a protective immune response. Experiments have shown that the nanoemulsion added to the hepatitis B surface antigen (HBsAg) and administered intranasally was a safe and effective vaccine against hepatitis B. Drop sizes of the nanoemulsion were not greater than 1000 nm. Aqueous phase of the nanoemulsion may contain PBS buffer. A suitable organic solvent is e.g. ethanol, acetone, formic acid. The oil phase of the nanoemulsion-based vaccine can be chosen from animal, plant, natural, synthetic, silicone oils, e.g. dimethylpolysiloxane. One example of the non-ionic detergent is e.g. tyloxapol and cationic is e.g. cetylpyridine chloride (CPC). The emulsion can be administered intranasally. Such administration can also include contacting with oral or bronchial mucosa and other epithelia. Nanoemulsion of the invention should kill or inactivate the ESV virus to a traceable level or induce a protective immune response on a traceable level.

The application WO2009131995 A1 relates to methods, compositions and kits to induce an immune response to a flu virus in humans. Methods include administration of vaccines in the form of nanoemulsion, whereas the vaccine as an oil-in-water nanoemulsion comprises drops having a diameter of approximately or less than 1000 nm. Nanoemulsion consists of an aqueous phase, at least one oil, e.g. dimethylpolysiloxane, at least one cationic detergent, e.g. cetylpyridine chloride (CPC), a non-ionic detergent, e.g. tyloxapol, at least one organic solvent (e.g. ethanol, acetone or formic acid) and at least one immunogen, recombinant protein or a combination thereof. Optionally, the nanoemulsion can also comprise a chelating agent. Composition of the nanoemulsion according to the invention serves as a vaccine adjuvant. Nanoemulsion vaccine adjuvant can be combined with an antigen or may be administered sequentially with an antigen. After administering the vaccine in the form of nanoemulsion, a human or animal produces a protective immune response. The vaccine can be directed against pathogens, such as a bacterium, fungus, protozoa or virus, such as a flu virus.

Patent application WO2017196979 provides compositions containing adjuvant emulsions and one or more active compounds or substances formulated for infusions or injections (e.g. using needles and syringes), as well as methods of formulating and use thereof (e.g. as a medical composition for injection (e.g. a vaccine). The adjuvant emulsion in immunogenic composition according to the invention comprises a cationic lipid with a polar domain and a two-chain hydrophobic group attached to the polar portion and a non-ionic detergent and an organic solvent. In another embodiment, the emulsion for injections additionally comprises oil and water. In another embodiment, the composition for injections was an oil-in-water emulsion. The present invention is not limited by the type of cationic lipid used, for example dimethyldioctadecylammonium chloride (DODAC). One example of the non-ionic detergent is tyloxapol. Also, the present invention is not limited by the antigen or immunogen used, and exemplary antigens and/or immunogens included inactivated pathogens, isolated and/or recombinant peptides, proteins.

SUMMARY

It is an object of the present invention to develop a veterinary vaccine of a fixed composition, comprising nanoadjuvant as an oil-in-water emulsion as well as surface antigens of C. difficile bacteria based on sequences of two proteins: 71 kDa and M24 protein, which have not yet been described in literature as potential components of a vaccine. Those proteins have been selected by the Applicant through the study on immunoreactivity of blood serum of patients with CDI, and cord blood serum. Using cord blood serum for this purpose enables finding new proteins with highly protective properties.

Available therapies using therapeutic antibodies were based on the entire bacterial cell and therefore, the fraction of therapeutically-active antibodies was very low in such preparations. However, focusing on selected protective proteins and their epitopes, as in the solution provided by the Applicant, enables a significant increase of this active fraction for a therapeutic effect. Additional components of the vaccine serving to enhance its effect are A and B toxins of *Clostridium difficile* bacteria and immunomodulating compounds belonging to the group of surface antigens, such as, without limitation, monophosphorylated lipid A (MPL), polysaccharides, teichoic and lipoteichoic acids. Those components are already used in vaccines or researched for such use.

The invention relates to a vaccine comprising nanoadjuvant in the form of an oil-in-water emulsion and immunostimulating components, characterised in that it comprises epitopes of new surface proteins from *Clostridium difficile* in a conjugate with carrier proteins and *Clostridium difficile* toxins. Preferably, the emulsion consists of synthetic oil. Preferably, surface proteins of *Clostridium difficile* are the 71 kDa protein of SEQ ID No. 1 and aminopeptidase M24 of SEQ ID No. 2.

Preferably, *Clostridium difficile* toxins are TcdA and TcdB toxin.

In addition to synthetic oil as a nanoadjuvant, the vaccine preferably comprises an organic solvent, a non-ionic detergent, a cationic detergent and ultrapure water.

Dimethylpolysiloxane is a preferred synthetic oil.

It is preferred that the organic solvent is chosen from the group consisting of ethanol, acetone, formic acid.

Preferably, the non-ionic detergent was chosen from the group consisting of polyoxyethylene sorbitol monooleate, tyloxapol.

Preferably, the cationic detergent is chosen from the group consisting of cetylpyridine chloride, benzyldimethyldodecylammonium chloride, cetylpyridine bromide, benzyldimethylhexadecylammonium chloride or cetyltrimethylammonium chloride.

Preferably, nanoadjuvant components are combined in the ratio of 60-70% oil, 4-8% non-ionic detergent, 1-3% cationic detergent, 5-10% organic solvent and 15-25% ultrapure water.

Preferably, immunostimulating components are antigens of probiotic bacteria, such as polysaccharides, teichoic acids, lipoteichoic acids, proteins, peptidoglycan, glycolipids, lipopolysaccharides, monophosphorylic lipid A, glycoproteins, bacteriocins, DNA, RNA, enzymes, peptides and other molecules secreted to the medium.

Preferably, the vaccine is administered parenterally and/or intramucosally.

Another object of the invention is the vaccine as described above for the use in the treatment of C. difficile infections in animals.

Preferably, the treated animals were birds and mammals.

Yet another subject of the invention is the use of the vaccine described above to produce C. difficile-specific antibodies.

Preferably, the C. difficile-specific antibody is an IgY class antibody.

In the method of obtaining the emulsion known as a nanoadjuvant, silicone oil, dimethylpolysiloxane (Sigma CAS Number 9016-00-6) with its viscosity similar to soybean oil (12,500 cSt (25° C.)), were used. Dimethylpolysiloxane is not limiting in the preparation of nanoadjuvants for vaccines according to the invention. Silicone oils with other parameters can prove to be more useful and increase the efficiency of nanoadjuvants in the process of inducing antigen-presenting cells. The use of silicone oil causes that the composition does not contain traces of protein, which are present in nanoadjuvant when using vegetable oil.

Using such a composition of vaccine for the immunization of birds and mammals, e.g. hens or cows, has not been yet described and has multiple advantages. The described vaccine can be used parenterally and intramucosally, and its manufacturing is not complicated, it does not contain a live pathogen, so it is safer, it does not contain a toxic adjuvant and allows obtaining a large fraction of specific therapeutic antibodies in a hen or cow that has been immunized by vaccination.

DETAILED DESCRIPTION OF EXEMPLARY ARRANGEMENTS

Figure 1:
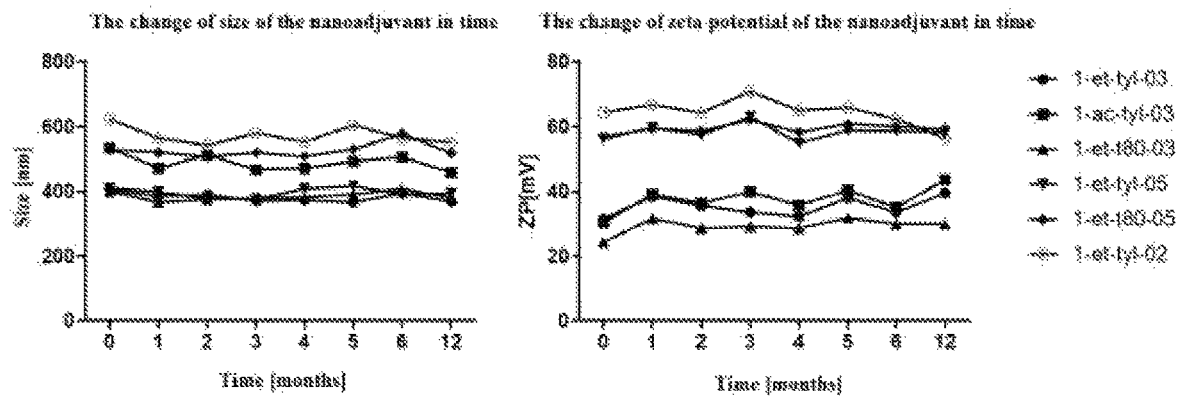
FIG. 1. shows the change of physicochemical properties of the nanoadjuvant during twelve months of observation. Changes of sizes and zeta potential of nanoadjuvant vesicles were analysed.
Figure 2:
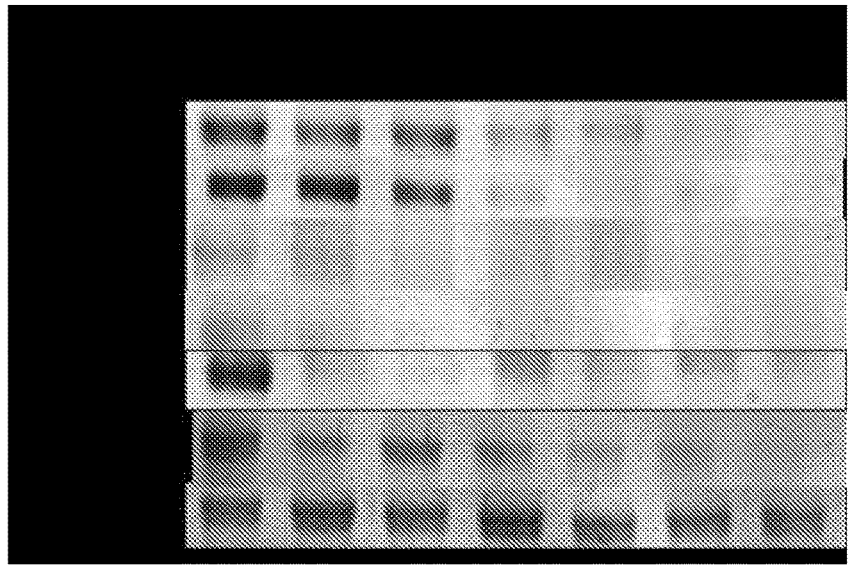
FIG. 2. shows pictures of bands after polyacrylamide gel electrophoresis (12% SDS-PAGE) with samples of the nanoadjuvant with the model OVA antigen applied, illustrating the durability of the antigen in nanoadjuvant after 6 months of storing under various temperature conditions.
Figure 3:
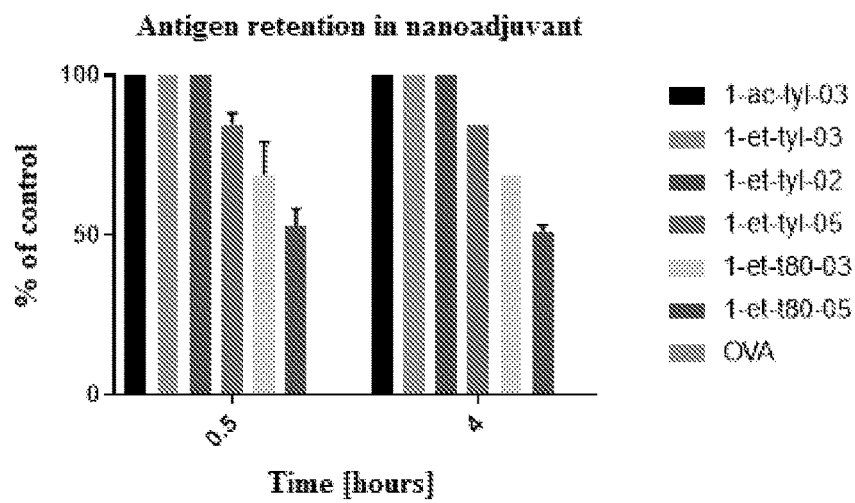
FIG. 3. shows a graph of antigen release kinetics from nanoadjuvant drops after 0.5 h and 4h.

The veterinary vaccine of the invention consists of:
a) a nanoadjuvant that consists of the following components: synthetic oil (as an example and not limitation, dimethylpolysiloxane), an organic solvent (as an example and not limitation, ethanol, acetone, formic acid), a non-ionic detergent (as an example and not limitation, polyoxyethylene sorbitol monooleate, tyloxapol), a cationic detergent (as an example and not limitation, cetylpyridine chloride, benzyldimethyldodecylammonium chloride, cetylpyridine bromide, benzyldimethylhexadecylammonium chloride or cetyltrimethylammonium chloride) and MiliQ water.
The composition of nanoadjuvants is not limited to substances mentioned above.
The nanoadjuvant components are combined in the ratio of 60-70% oil, 3-8% non-ionic detergent, 1-3% cationic detergent, 5-10% organic solvent and 15-25% water.
Exemplary composition of the nanoadjuvant: 65% dimethylpolysiloxane (oil), 5% tyloxapol (non-ionic detergent), 1% benzyldimethyldodecylammonium chloride (cationic detergent), 8% ethanol (organic solvent), 21% water. The proportions mentioned above may change.
Nanoadjuvants of the invention are in the form of oil-in-water emulsion with the diameter of drops smaller than 1 μm. Its surface layer consists of ionic and non-ionic detergents with oil being inside the drop.
b) epitopes of *Clostridium difficile* surface proteins, 71 kDa proteins and M24 aminopeptidases in a conjugate with a carrier protein. Exemplary amino acid sequences of 71 kDa protein epitopes: ATGKKGSETPTGKTKV (SEQ ID No. 16), VNKIKNRPYYKGNIPG (SEQ ID No. 23), SRKNTLGYFVNNKLVK (SEQ ID No. 24), GTYQKNSWLKVNGKMY (SEQ ID No. 7), QTGWQEKNGKKYYLGS (SEQ ID No. 6), TGWK- TENGKKYYVKSD (SEQ ID No. 17), NKKYYLGTDGARVSGW (SEQ ID No. 18), FDTAKKISSVGNWNAD (SEQ ID No. 19), EFRVAT (SEQ ID No. 8), KVNGKM (SEQ ID No. 9) and WQEKNGKKYY (SEQ ID No. 10) and M24 proteins: FISGFNGSAGTVIVTK (SEQ ID No. 20), REGAT-LAEKKLSKKGIK (SEQ ID No. 21), KKGIK-IEYQYDLIDGI (SEQ ID No. 22), LREKMSEKGT-STHVIT (SEQ ID No. 12), MGIDYQCGTGHGIGFV (SEQ ID No. 13), KKGIK (SEQ ID No. 14) and KGTSTHVIT (SEQ ID No. 15) and their modifications including but not limited to: biotinylation, flanking of sequences with amino acids, substituting amino acids with other amino acids that change the sequence, whereas no more than 50% of amino acids of the initial sequence have been modified.

c) *Clostridium difficile* toxins—TcdA and TcdB toxin. Those are the components responsible for symptoms typical to the CD infection. High level of those toxins leads to the onset of inflammatory bowel disease and influences the duration of diarrhoea. It has been also proved that a high level of IgG antibodies against the TcdA toxin prevents the development of CDI, and administering the anti-TcdA monoclonal antibody to mice protected them against the infection [Voth D E, Ballard J D. *Clostridium difficile* Toxins: Mechanism of Action and Role in Disease. *Clinical Microbiology Reviews*. 2005; 18(2):247-263. doi: 10.1128/CMR.18.2.247-263.2005]. There are studies on the use of those toxins in vaccines.

d) other immunomodulating agents, including probiotic bacteria antigens of *Lactobacillus, Bifidobacterium, Akkermansia* or *Faecalibacterium* species, such as: polysaccharides, teichoic acids, lipoteichoic acids, proteins, peptidoglycans, glycolipids, lipopolysaccharides, monophosphorylic lipid A, glycoproteins, bacteriocins, DNA, RNA, enzymes, peptides and other particles secreted to the medium. Other immunomodulating components not derived from bacteria, including cytokines and modifications thereof, nonimmunogenic peptides, lipids, polar proteins. Those components serve to enhance the effect of the vaccine.

The invention also provides the method of producing vaccinations according to the invention, including the following steps:

a) preparation of nanoadjuvants by heating the mixture of a non-ionic detergent, cationic detergent, organic solvent and water to approximately 65° C. in water bath;

b) transferring to the polyethylene Luer lock syringe while oil is drawn into the second syringe. Both syringes are connected to the emulsifier;

c) emulsifying by actuating the syringe pistons. Emulsification is performed until drops of desired size are obtained. Nanoadjuvant can also be obtained by using a mechanical lab emulsifier;

d) prepared nanoadjuvants are diluted with MiliQ water to obtain concentration of 60% and it is transferred to glass containers sealed with a plug;

e) thus prepared nanoadjuvants are stored in a refrigerator at 4° C.

Epitopes of surface proteins are prepared by the method described in the embodiments below.

Toxins are obtained commercially.

Additional immunostimulating elements could be both isolated from microorganisms and obtained commercially.

The vaccine is prepared by simply mixing the above components in suitable proportions. Due to the manufacturing technology employed, it is very easy to manipulate the content of the formulation for injections in order to obtain antibodies adjusted to the changing strains, should they develop resistance. It is possible to use another epitope from a group of already identified and described epitopes. The procedure of obtaining conjugates is fast and inexpensive.

Exemplary composition of a single dose of the vaccine includes: (0.5-1.5 ml)—conjugates (epitope and carrier protein (0.5-1.0 mg), A and B toxins (0.5-1.0 mg) of *C. difficile* bacteria with the nanoadjuvant (0.001%-10%).

The essence of vaccine efficacy is the nanoadjuvant, which is characterised in detail by measuring pH, calculating the value of hydrophilic-lipophilic balance (HLB) of the mixture, assaying the zeta potential and drop size. Table 1 shows data for 6 exemplary nanoadjuvants. pH of nanoadjuvants present in the vaccine of the invention, depending on the composition, ranges from 3.5 to 6.8. HLB values of nanoadjuvants present in the vaccine of the invention, depending on the composition, range from 7.82 to 8.74. The zeta potential (ZP) and drop sizes of nanoadjuvants were established using Zetasizer Nano ZS (Malvern Instruments). Prior to the measurement, nanoadjuvants were diluted to the concentration of 0.1% in 1 mM of HEPES buffer (4-(2-hydroxyethyl)-1-piperazineethanesulfonic acid) of pH 7. The size of nanoadjuvant drops in the vaccine of the invention ranges from 320.5 nm to 1000 nm and depends on the content of the mixture. The zeta potential of nanoadjuvants ranges from +8.55 mV to +71.7 mV and depends on the content of the mixture.

Example 1—Stability of Nanoadjuvants

The stability of nanoadjuvants was determined by visual inspection and by assaying drop sizes and zeta potential during the period of 0, 1, 2, 3, 4, 5, 6 and 12 months, as shown in FIG. 1. Visual inspection includes assessing the degree of decomposition, also called "emulsion ageing", namely looking for the signs of delamination, sedimentation or creaming.

Visual inspection and measurement of the size and zeta potential indicate that stored nanoadjuvants are stable for at least a year. Measurements of drop sizes and their zeta potential did not show significant differences.

TABLE 1

Physicochemical properties of 6 exemplary nanoadjuvants

| Name | ZP (mV) | Size (nm) | HLB |
|---|---|---|---|
| 1-et-tyl-03 | +31.6 | 405 | |
| 1-ac-tyl-03 | +30.4 | 534 | |
| 1-et-t80-03 | +24.4 | 400 | |
| 1-et-tyl-05 | +56.2 | 411 | 8.40 |
| 1-et-t80-05 | +56.9 | 529 | 8.67 |
| 1-et-tyl-02 | +64.4 | 624 | |

Example 2—Interaction of Nanoadjuvants with the Model Antigen (Ovoalbumin)

Figure 4:
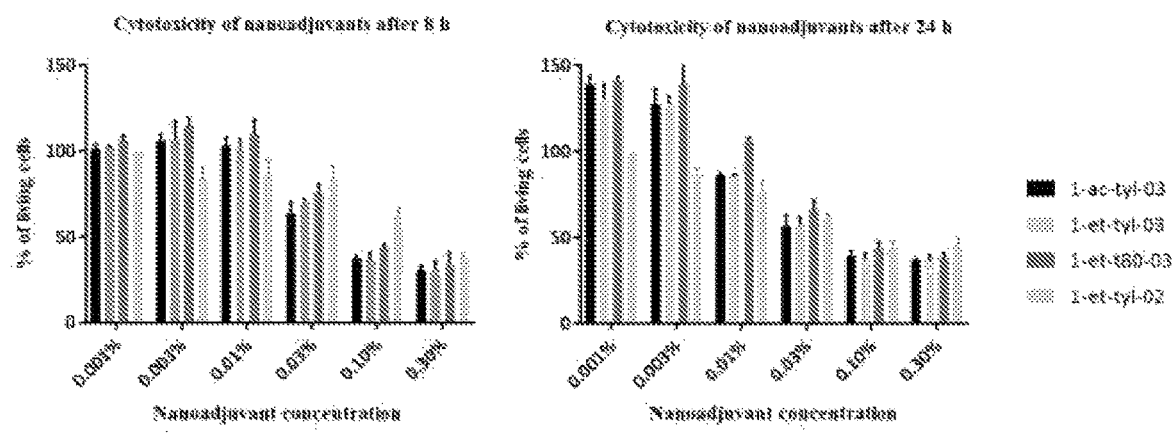
FIG. 4. shows a graph illustrating the cytotoxicity of nanoadjuvants against BMDM line after 8h and 24h of incubation. The result was shown as control % which consisted of living BMDM cells not treated with the nanoadjuvant.

The interaction between the protein model antigen and the nanoadjuvant is analysed. The effect of adding the protein antigen on the size of nanoadjuvant drops was analysed using a Zetasizer Nano ZS device. Chicken egg albumin was selected as the model antigen (ovoalbumin, OVA). 3 minutes before the measurement, the nanoadjuvant was mixed with the OVA (1 mg/ml) solution to a final concentration of 0.1% (v/v) of nanoadjuvant and 3.33 μg/ml of OVA. Nanoadjuvants which are the main component of the vaccine of the invention interact with the antigen, which is depicted by the increase of drop sizes and the decrease of zeta potential values. It seems that nanoadjuvants with lower potential interact with antigen more easily than those with higher potential. Exemplary results for 6 selected nanoadjuvants were shown in Table 2.

TABLE 2

Comparison of the properties of nanoadjuvants before and after administration of the model antigen

| Name | ZP before OVA is added | ZP after OVA is added [mV] | Size before OVA is added [nm] | Size after OVA is added [nm] |
|---|---|---|---|---|
| 1-et-tyl-03 | +31.6 | +9.8 | 405 | 7745 |
| 1-ac-tyl-03 | +30.4 | +30 | 534 | 3962 |
| 1-et-t80-03 | +24.4 | +9.09 | 400 | 4462 |
| 1-et-tyl-05 | +56.2 | +34.7 | 411 | 2158 |
| 1-et-t80-05 | +56.9 | +25.1 | 529.4 | 614.4 |
| 1-et-tyl-02 | +64.4 | +39.3 | 623.6 | 8392 |

Stabilizing properties of the nanoadjuvant against the antigen were analysed. The model protein antigen (OVA) was incubated with the nanoadjuvant for 6 months under the following conditions: 4° C., room temperature, and 37° C. During the experiment, subsequent samples were collected at regular intervals. The antigen integrity was analysed by electrophoresis in 12.5% polyacrylamide gel under denaturing conditions (SDS-PAGE, BioRad), and results are shown in FIG. 2. The same volume of mixture nanoadjuvant/antigen was applied to each well, and also the control sample in the form of antigen alone that was stored in a similar way. Analysed nanoadjuvants influence the stability of the protein antigen in different ways. For example, nanoadjuvants 1-et-tyl-03, 1-ac-tyl-03 and 1-et-tyl-02 do not significantly influence the antigen even after 6 months of storing at 4° C. It is a very crucial feature of a vaccine carrier.

Kinetics of releasing the model antigen from nanoadjuvant drops was analysed. A mixture of 60% nanoadjuvant and OVA (1 mg/ml) was prepared and it was incubated at room temperature for 5 minutes. The mixture was diluted 36 times to obtain the final concentration equal to 4 ml in 1 mM solution of HEPES at pH=7. The solution was centrifuged and the supernatant was discarded in order to remove the antigen, which was not absorbed to the inside of vesicles. The residue was suspended again in 4 ml of 1 mM HEPES at pH=7. Then a sample of supernatant (2 ml) was collected every 12 h from the previously centrifuged mixture, in which the protein content was then assayed using the BCA method. The collected supernatant was replaced by a fresh solution of 1 mM HEPES at pH=7 (2 ml). Release kinetics of the antigen is shown in FIG. 3. Nanoadjuvants differ from each other in terms of the amount of closed antigen and its release kinetics. For example, two nanoadjuvants 1-ac-tyl-03, 1-et-tyl-03 and 1-et-tyl-02 encapsulate 100% of the protein antigen and retain it inside for a long time. The nanoadjuvant 1-et-t80-05 encapsulates in its drops approximately 50% of the antigen and loses a portion of the antigen over time. Measurements made after 24 hours did not differ from the result for 4 hours (not shown in the graph).

Example 3—Bioadhesion of Nanoadjuvants—Interaction with Mucin

Bioadhesion properties of nanoadjuvants were studied by analysing the interaction of nanoadjuvants with mucin (a protein component of mucus lining the mucosa of nose) using a Zetasizer Nano ZS device. To the nanoadjuvant of 0.1% (v/v) concentration in 1 mM HEPES pH=7, the mucin solution was added in order to obtain the final concentration of 47.6 μg/ml. Then the vesicle size of the nanoadjuvant and its zeta potential was measured. The results are shown in Table 3.

TABLE 3

Change of physicochemical properties after mucin is added

| Name | ZP before mucin is added [mV] | ZP after mucin is added [mV] | Size before mucin is added [nm] | Size after mucin is added [nm] |
|---|---|---|---|---|
| 1-et-tyl-03 | +31.6 | −25.3 | 405 | 401 |
| 1-ac-tyl-03 | +30.4 | −26.1 | 534 | 489 |
| 1-et-t80-03 | +24.4 | −22.1 | 400 | 418 |
| 1-et-tyl-05 | +56.2 | −28.5 | 411 | 441 |
| 1-et-t80-05 | +56.9 | −19.9 | 529 | 563 |
| 1-et-tyl-02 | +64.4 | −16.4 | 624 | 649 |

Nanoadjuvants interact with mucin, which is indicated by the strong decrease in zeta potential of nanoadjuvants (on average from +43.98 mV to −23.05 mV). Not all nanoadjuvants interact with mucin in the same way and the nature of this interaction depends on the zeta potential of the nanoadjuvant which results from the type of cationic detergent used. Choosing the right detergent, and therefore the zeta potential, can be used to modulate biological properties of the formulation.

Example 4—Cytotoxicity of Nanoadjuvants Against Macrophage Lines

Cytotoxicity of nanoadjuvants of various concentrations was analysed using macrophage lines obtained from the bone marrow of BALB/c mice (BMDM line—Bone Marrow-Derived Macrophages). The test was carried out on a 96-well plate in which 2×104 cells/well in DMEM/F medium with an addition of 10% FBS and antibiotics were seeded 48 h earlier. The cytotoxicity of nanoadjuvants after 8 h and 24 h (FIG. 4) of incubation was studied using the SRB test (Sulforhodamine B colorimetric assay). Nanoadjuvant dilutions used were 0.001%, 0.01%, 0.1% and 1% (v/v). Untreated cells were used as a control.

In low concentrations, namely up to 0.01%, after 8 h of incubation nanoadjuvants do not show cytotoxic activity against macrophage cells. During the incubation lasting 24 h with nanoadjuvants concentrations of 0.01%, the increase of macrophage growth is present. The highest cytotoxicity against analysed cells is shown by the nanoadjuvant of concentration equal to 0.1%, further increase in nanoadjuvant concentration does not have any effect.

Figure 5:
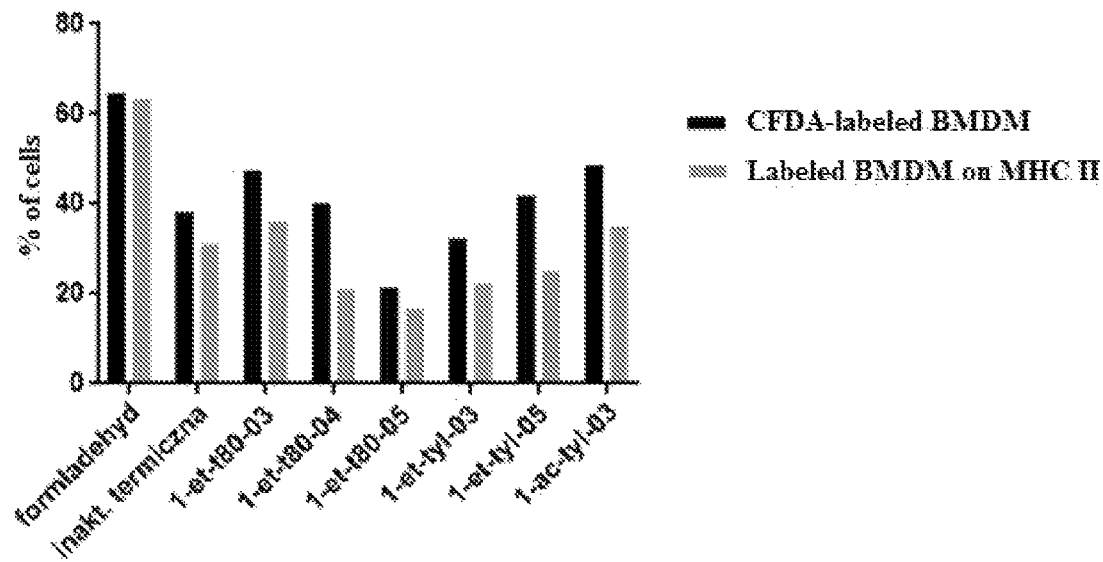
FIG. 5. shows a graph illustrating the effect of nanoadjuvant on absorbing *Clostridium difficile* by BMDM line cells. Positive control included formaldehyde-inactivated *C. difficile* cells and negative control included thermally inactivated *C. difficile* cells. Line cells were incubated with bacterial cells for 4h and were subsequently analysed using a cytometer.

Example 5—Effect of Nanoadjuvants on Antigen Uptake by Macrophages and Expression of the MHC II Protein The effect of nanoadjuvants on the uptake of antigen in the form of *Clostridium difficile* R20291 by macrophages was analysed using BMDM line and flow cytometry FACSCalibur (BD Biosciences). Cells were seeded on a 12-well plate with 0.5 m cells/well in DMEM/F medium, adding 10% FBS and antibiotics the day before the experiment. At the same time, the antigen in the form of *Clostridium difficile* R20291 bacteria stained with CFDA-SE (BioRad) dye according to manufacturer instructions was prepared and incubated overnight in individual nanoadjuvants of 10% concentration (v/v). Thermally inactivated antigen and 1% formaldehyde were used as a control. Thermal inactivation included incubating the sample for 30 min at 71° C., then for 20 min at 85° C. After washing with 3×PBS, antigen was added to BMDM cells and incubated for 4 h at 37° C. After incubation, 100 µl of supernatant was sampled to assay the cytokine concentration. Cells were collected and transferred to a 96-well plate in order to stain proteins of WIC II class using specific anti-mouse antibodies WIC class II conjugated with APC (eBioscience). Staining was carried out according to the instructions of the manufacturer. Then the cells were analysed using a flow cytometer (FL1 channel for CFDA and FL3 for APC). Similarly, a control experiment was carried out, in which cells were stimulated with the same antigen at 4° C. in order to rule out any possible non-specific interactions. Non-specific interactions were not found. Results for assays at 37° C. were summarized in FIG. 5. Selected nanoadjuvants (1-ac-tyl-03, 1-et-t80-03, 1-et-tyl-05) induce the antigen uptake of macrophages. At the same time, 1-et-t80-03 and 1-ac-tyl-03 activate the expression of proteins of WIC class II against the thermally inactivated control.

Example 6—Induction of Cytokines by the Nanoadjuvant in Combination with LPS 0.1×106 of macrophages (BMDM from BALB/c mice) were seeded on a 96-well plate in 200 µl of DMEM/F medium with 10% FBS, incubated overnight, then the medium was collected and replaced to 180 µl of fresh medium. 10 µl of nanoadjuvant (20× concentrated) was added so that the concentration is 0.001%, 0.003%, 0.01% or 0.03%, respectively. Then to each of the wells was added 10 µl LPS 20× concentrated (Invivogen) to obtain the final concentration equal to 1 ng/ml. Control samples: nanoadjuvant alone without LPS, LPS alone without nanoadjuvant, untreated cells. Cells were incubated for 24 h in an incubator and then supernatants were collected in order to assay the cytokine level. TNFα level was measured using the ELISA MAX Mouse TNFα kit (BioLegend), according to the instructions of the manufacturer. The experiment was repeated three times.

Figure 6:
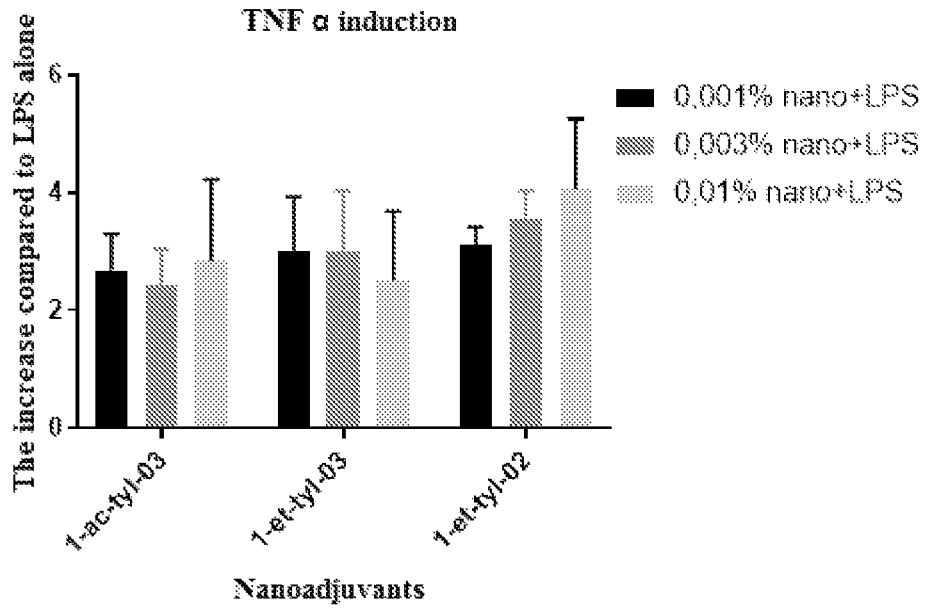
FIG. 6. shows a graph illustrating the induction of TNFα in macrophage cells by the nanoadjuvant of various concentration and subactivating concentration of LPS (1 ng/ml). The increase of TNFa production in macrophages after 24h of incubation with a formulation of nanoadjuvant+LPS relative to samples treated with LPS alone was shown.

Nanoadjuvants given to macrophages do not induce the production of the proinflammatory cytokine (results not shown). Adding an antigen in the form of LPS to the nanoadjuvant causes a strong induction of the proinflammatory cytokine production—a 2 to 4-fold increase relative to the level induced by LPS (FIG. 6). The effect depends on the nanoadjuvant concentration. The above experiment confirms the adjuvant activity of nanoadjuvants of the invention.

Example 7—Effect of Nanoadjuvants on Absorbing Antigens of Epithelial Cells

Figure 7:
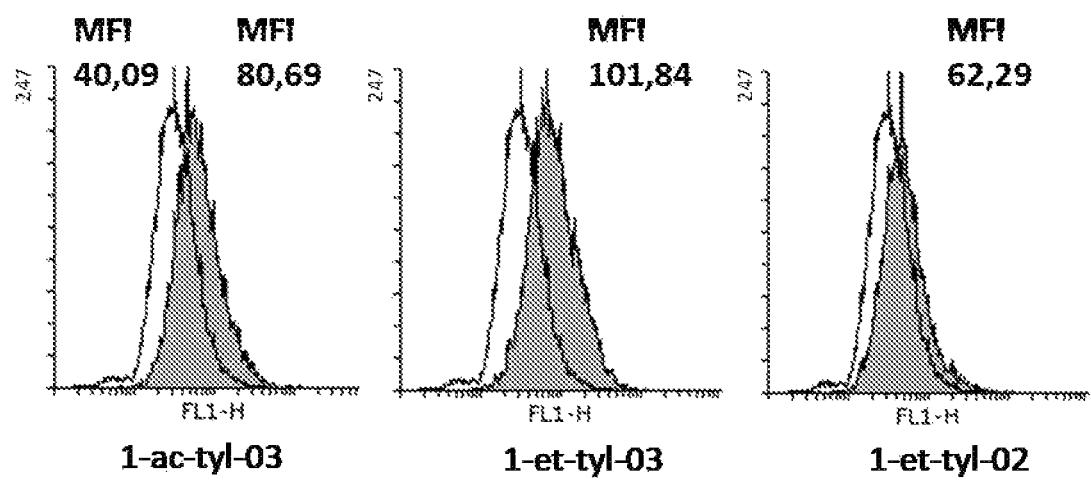
FIG. 7. shows the effect of nanoadjuvant on antigen absorption by RMPI2650 cells. Cells were incubated for 4h with DQ-OVA with or without the addition of the nanoadjuvant (0.06%). The level of antigen absorption was studied using a flow cytometer. White histograms-DQ-OVA only, grey histograms-DQ-OVA with the nanoadjuvant.

The effect of the added nanoadjuvant on the uptake of antigen by respiratory epithelial cells was analysed. For this, a cell line RPMI 2650 (ATCC® CCL-30™) derived from a human nasal septum and DQ-OVA, a protein which shows fluorescent properties after digestion by intracellular proteases, was used. 0.2×106 cells were plated to a well of a 24-well plate in 500 µl of full medium with 2.5% FBS. Cells were incubated for 4 h with or without NAC and 10 µg/ml of DQ-OVA (cat. D12053, Thermo Fisher Scientific). Cells were washed twice with warm PBS and separated by trypsinization. Then cells were analysed using FACSCalibur Cell Analyzer (BD Biosciences). Results shown in FIG. 7 are representative for two experiments. Adding the nanoadjuvant in a concentration of 0.6% causes the induction of DQ-OVA absorption (1-et-tyl-03 being the strongest, then 1 ac-tyl-03 and 1-et-tyl-02).

Example 8—Analysing the in Vivo Tolerance of the Nanoadjuvant

Figure 8:
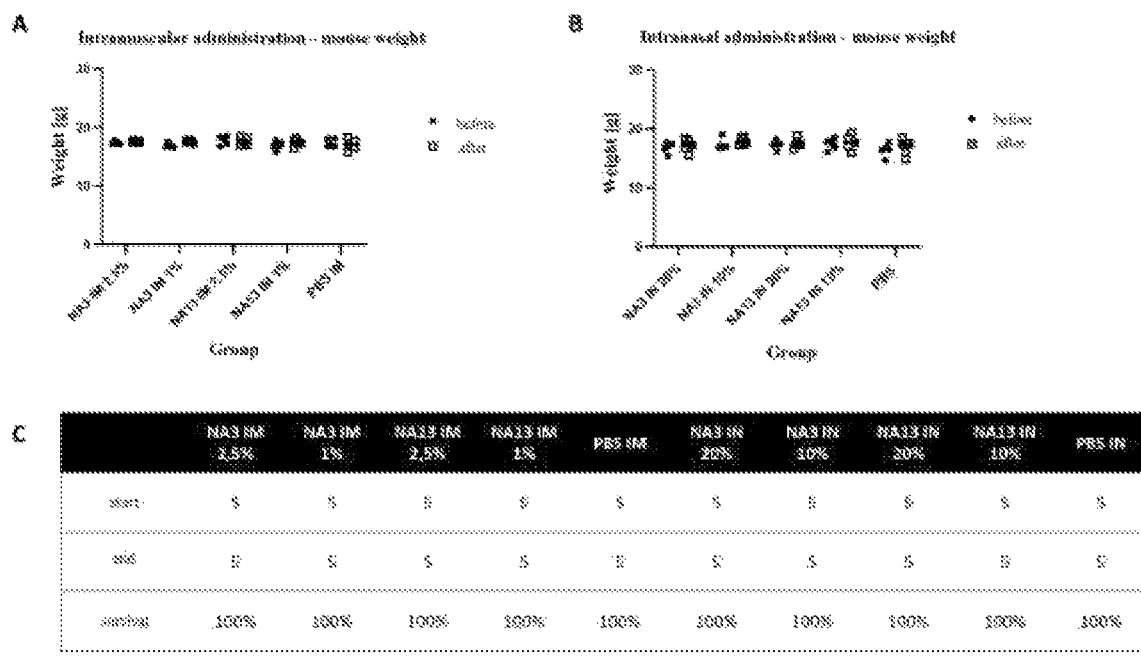
FIG. 8. shows the result of studying nanoadjuvants tolerance in mice. 8A-change of mice weight with nanoadjuvant administered intramuscularly; 8B-change of mice weight with nanoadjuvant administered intranasally; 8C-mice survival rate.

Nanoadjuvant tolerance of C57BL/6 strain in intranasal and intramuscular administration to mice was analysed. Nanoadjuvant was administered to mice (n=5) intramuscularly (2.5% and 1%) and intranasally (20% and 10%). The mice were observed for adverse effects for 7 days. No changes in mice behaviour or weight were observed (FIG. 8). All tested mice survived the experiment. Histopathologic specimens collected from the place of nanoadjuvant administration have not shown significant deviations, only an inflammatory infiltration of small intensity, which passes after a few days. Properties of new *Clostridium difficile* antigens are described below:

Example 9-71 kDa Protein

The immunoreactive 71 kDa protein was identified using peripheral blood serum taken from a patient with a confirmed *Clostridium difficile* infection. Culture of the clinical strain Cd20 (ribotype 027) (strain deposited in the Polish Collection of Microorganisms as PCM 2628) was carried out in liquid medium BHI (Brain-Heart Infusion) under oxygen-free conditions. 1 g of bacterial mass was extracted with 1 M LiCl (POCh) for 45 minutes at room temperature with stirring in order to isolate surface proteins [17]. The bacterial mass was centrifuged and the supernatant was dialysed to MQ water using a dialysis membrane with MWCO=6 000-8 000 Da (Roth). The supernatant was filtered off (Amicon ultra-15, Merck Millipore) in order to thicken the isolated proteins. Proteins were analysed by one and two-way electrophoresis and immunoblotting using serum of *Clostridium difficile*-infected patient. The analysis allowed selecting proteins to be identified by the LC-MS-MS/MS method using an Orbitrap (Thermo) spectrometer and by comparing obtained peptides with data from NCBI and UniProt bases using MASCOT software. The result of this identification is a surface protein with a mass of 71.03 kDa and pI 8.95 (score 3014, sequence identity 60%).

The protein was subjected to a bioinformatics analysis in order to identify potential epitopes (determining the secondary and tertiary structure, analysing conservative domains, analysing the protein variation and its spread in other organisms). The sequence of the identified protein [18] is presented as SEQ ID No. 1. The nucleotide sequence of 71 kDa protein is however presented as SEQ ID No. 3.

The analysis of amino acid sequence variation using BLAST tool showed a strongly conserved nature of protein within *Clostridium* strains. The analysis of conserved domains was carried out in order to determine protein functionality. The analysis of conserved domains indicated a presence of a YkuD catalytic domain having a transpeptidase activity and domains responsible of binding a protein to the cell wall, which confirms the surface location of the protein.

Catalytic domain with a transpeptidase activity indicates that a protein can take part in peptidoglycan production. Blocking the activity of such protein, e.g. by antibodies, would cause the lack of growth and division ability of bacteria, therefore causing the removal of the infection.

Figure 9:
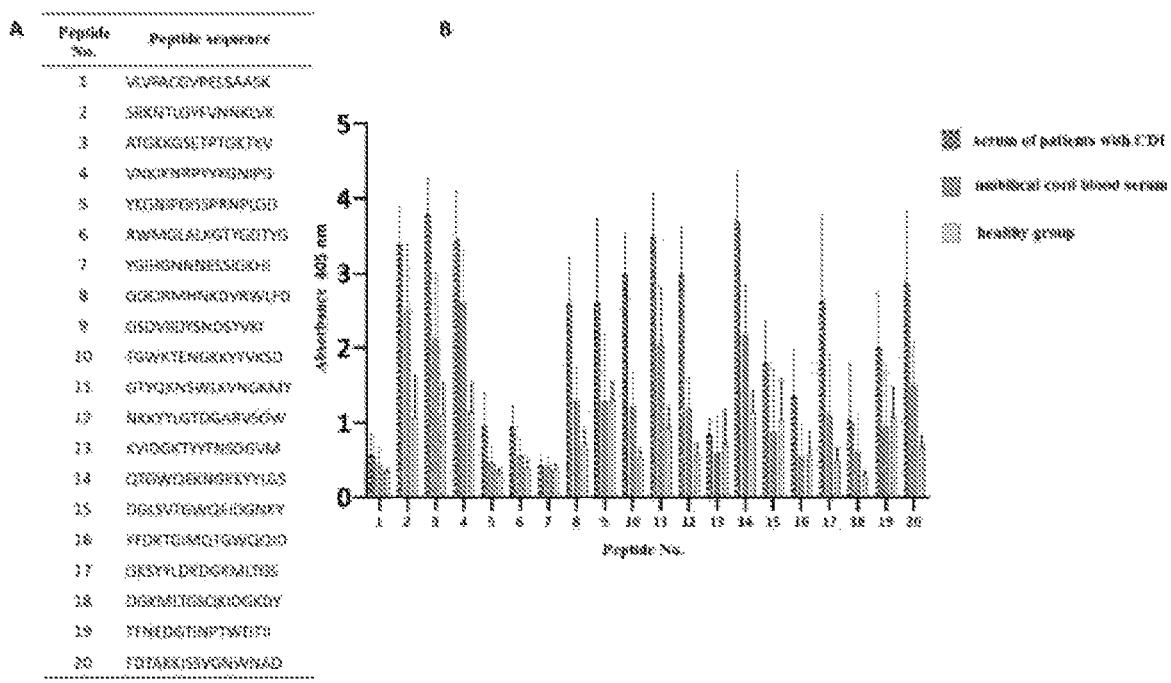
FIG. 9. The result of 71 kDa protein mapping. 9A—a list of peptides selected for the synthesis; 9B—the result of immunoreactivity test (ELISA) carried out on synthesised peptides.

Sequence analysis using software for determining epitopes for T and B cells and analysis of the protein model allowed choosing 20 peptides of 16 amino acids in length, which are potential epitopes, which were mapped using the PEPSCAN technique [4] (FIG. 9A). The synthesis of peptides was carried out on hydroxypropyl methacrylate pins (NCP, noncleavable peptide type) at room temperature under a fume hood. It was aimed at separated adding of selected amino acids until peptides of set length, oriented with the C-terminus towards pins, were obtained. After attaching all amino acids, blocked pendant groups in synthesised peptides were activated. Pins were then cleaned by methanol washing, dried out and prepared for the ELISA test.

The enzyme-linked immunosorbent assay ELISA was used to determine the immunoreactivity of peptides synthesized on pins. Pins were equilibrated in TBS-T buffer (Tris-HCl pH 7, Tween80), free spaces in pins were blocked (in order to avoid the non-specific binding of antibodies) during incubation in blocking buffer (TBST+1% BSA) for 1 hour at room temperature. They were incubated with primary antibodies (blood serum of patients with CDI) in 1:1000 dilution in TBS-T with 0.1% BSA for 2 h at room temperature. Then they were rinsed with TBS-T buffer and incubated with secondary antibodies (anti-human IgG) in a 1:10000 dilution in TBS-T for 1 hour at room temperature. Secondary antibodies were attached to the alkaline phosphatase and bound to primary antibodies and then washed as above. Subsequently, a colour reaction using an alkaline phosphatase substrate was performed. Staining intensity was measured using a spectrophotometer with 405 nm. After the colour reaction, pins were individually treated with a buffer with SDS.

High immunoreactivity (absorbance of over 2) of selected peptides indicates that antibodies directed against particular epitopes of 71 kDA protein are present in the blood of the patient. A slightly smaller titer of specific antibodies is present in cord blood serum and the lowest in blood serum of healthy participants. Reactive epitopes can be used in the production of diagnostic tests, vaccine or therapeutic antibodies.

Figure 10:
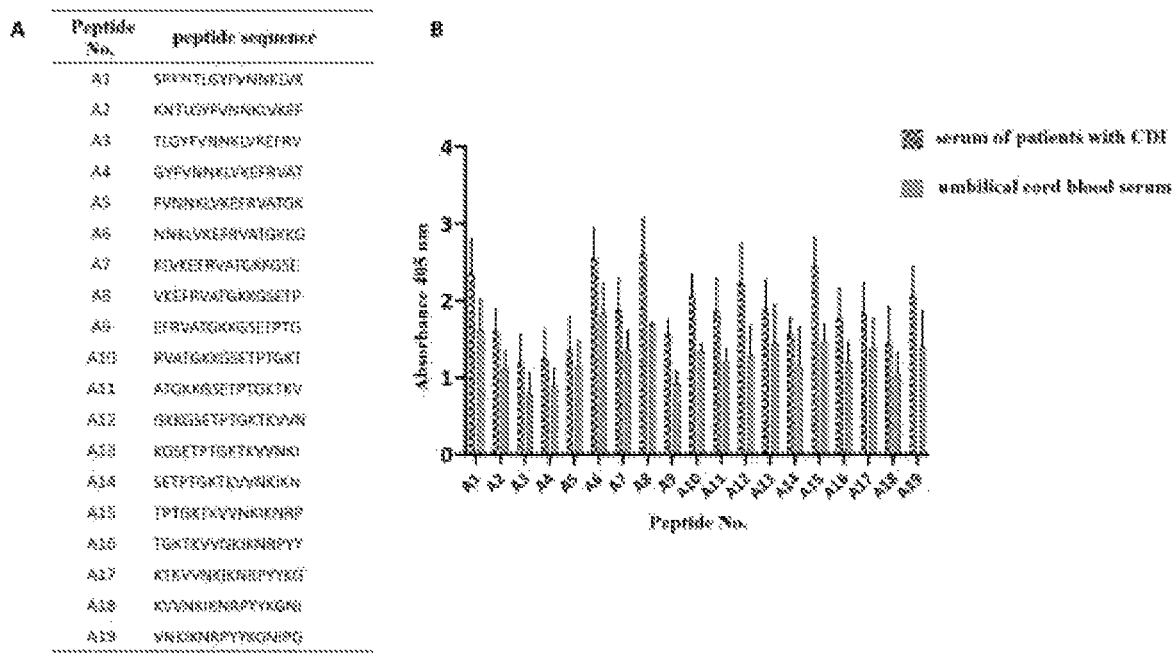
FIG. 10. The result of mapping a highly immunoreacitve region of 71 kDa protein. 10A—a list of peptides selected for the synthesis; 10B—the result of immunoreactivity test (ELISA) carried out on synthesised peptides.

The mapping of 71 kDa protein indicated the presence of at least several candidates for vaccinal epitopes (FIG. 9):

(2) SRKNTLGYFVNNKLVK } this highly active region was mapped in more detail
(3) TGKKGSETPTGKTKV
(4) VNKIKNRPYYKGNIPG
(11) GTYQKNSWLKVNGKMY
(14) QTGWQEKNGKKYYLGS Additional mapping of the region, consisting of peptide (2) to (4) was carried out (FIG. 10). Basing on the obtained results, sequences were selected for the analysis of minimal epitopes (peptides with the highest immunoreactivity):

NNKLVKEFRVATGKKSETP (SEQ ID No. 5)

QTGWQEKNGKKYYLGS (SEQ ID No. 6)

GTYQKNSWLKVNGKMY (SEQ ID No. 7)

Figure 11:
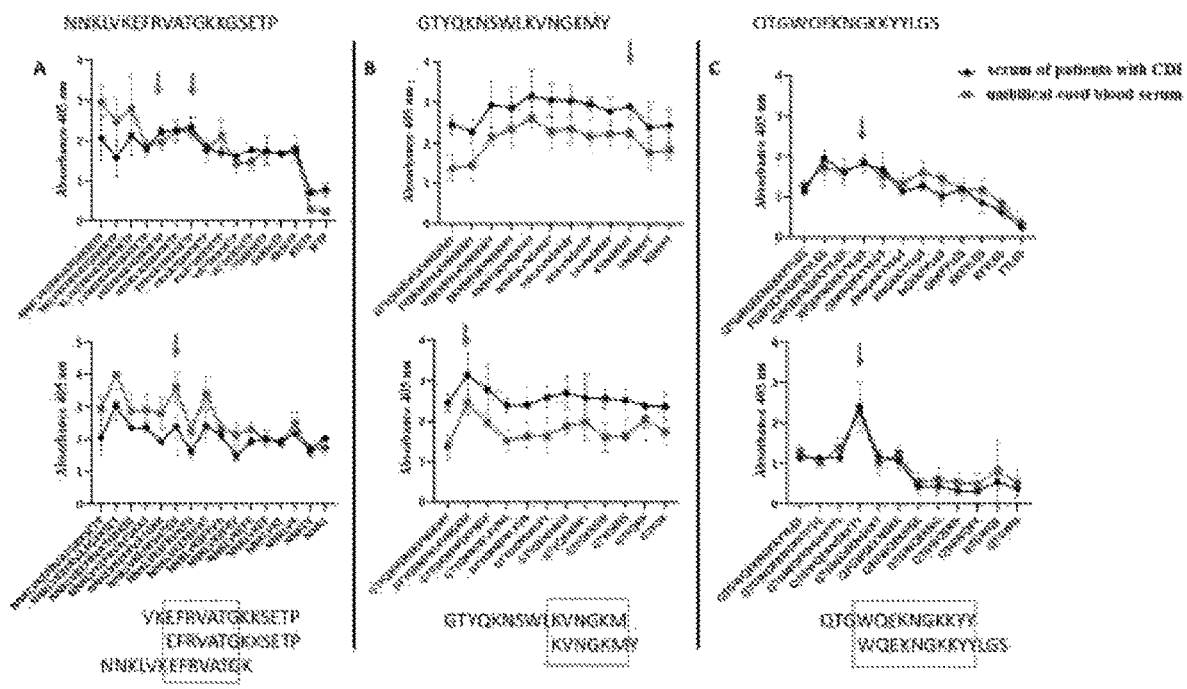
FIG. 11. selecting the shortest immunoreactive sequences (epitopes) of 71 kDa protein. The upper panel shows truncation from N-terminus; the lower panel from C-terminus. 11A—the truncation of NNKLVKEFRVATGKKSETP peptide (SEQ ID NO: 5); 11B—the truncation of QTGWQEKNGKKYYLGS peptide (SEQ ID NO:6); 11C—the truncation of GTYQKNSWLK VNGKMY peptide (SEQ ID NO:7).

Then the analysis of the shortest epitopes of 71 kDa protein was carried out (FIG. 11). It results in short immunoreactive amino acid sequences that are specifically recognized by antibodies. By using in the vaccine those epitopes alone, it is more potent and its production is cheaper.

Epitopes identified in 71 kDa protein are:

54EFRVAT59 (SEQ ID No. 8)

201KVNGKM206 (SEQ ID No. 9)

268WQEKNGKKYY277 (SEQ ID No. 10)

Example 10—M24 Peptidase

The immunoreactive peptidase M24 was identified using cord blood serum sampled from a healthy woman and proteins isolated from the clinical strain Cd27 (deposited in the Polish Collection of Microorganisms as PCM 2827). Culture of the clinical strain Cd27 (ribotype 027) was carried out in liquid medium BHI (Brain-Heart Infusion) under oxygen-free conditions. 1 g of bacterial mass was extracted with 1 M LiCl (Poch) for 45 minutes at room temperature with stirring in order to isolate surface proteins. The bacterial mass was centrifuged and the supernatant was dialysed to MQ water using a dialysis membrane with MWCO=6 000-8 000 Da (Roth) for 48 hours at 4° C., changing the water three times. The supernatant was filtered off (Amicon ultra-15, Merck Millipore) in order to thicken the isolated proteins. Proteins were analysed by one and two-way electrophoresis and immunoblotting. In order to analyse the immunoreactivity, proteins were subjected to immunoblotting using cord blood serum.

The analysis allowed for selecting proteins to be identified by the LC-MS-MS/MS method using an Orbitrap (Thermo) spectrometer and by comparing obtained peptides with data from NCBI and UniProt bases using MASCOT software. The result of this identification is a surface protein with a mass of 68.5 kDa and pI 5.11 (score 5102, sequence identity 72%).

The protein was subjected to a bioinformatics analysis in order to identify potential epitopes (determining the secondary and tertiary structure, analysing conservative domains, analysing the protein variation and its spread in other organisms). The identified protein sequence [19] is shown as SEQ ID No. 2 and the nucleotide sequence M24 as SEQ ID No. 4.

Analysis of the amino acid sequence variation using BLAST software showed that the sequence of peptidase M24 is conserved in *Clostridium difficile* strains. It shows low homology with other *Clostridium* species (27-63%, only for *Clostridium dakarense* 73%), human peptidase (35-40%) or selected bacteria belonging to human bacterial flora (23-63%). Sequence analysis using software for determining epitopes for T and B cells and the protein model analysis allowed choosing 21 peptides of 16 amino acids in length, which were potential epitopes, which were mapped using the PEPSCAN technique. The synthesis of peptides and immunoreactivity analysis were carried out in the same way as for the 71 kDa protein.

Figure 12:
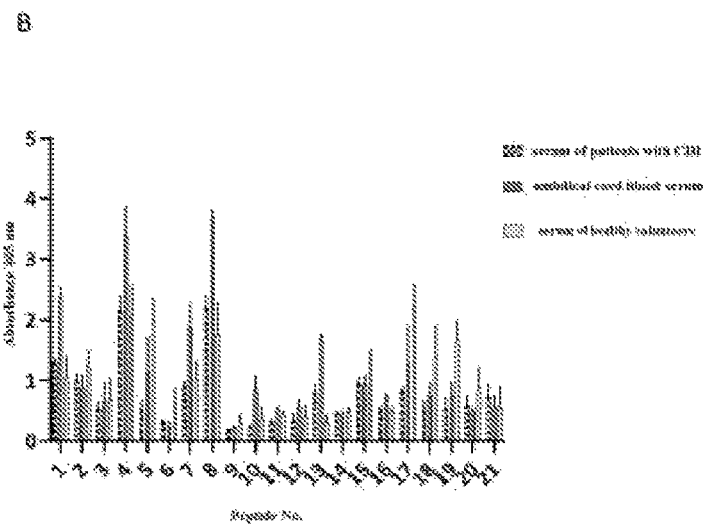
FIG. 12. The result of protein M24 mapping. 12A—a list of peptides selected for the synthesis; 12B—the result of immunoreactivity test (ELISA) carried out on synthesised peptides.

The mapping indicated the presence of at least a few candidates for vaccinal antigens, i.e. peptides with the highest immunoreactivity (FIG. 12):

REGATLAEKLSKKGIK (SEQ ID No. 11)

LREKMSEKGTSTHVIT (SEQ ID No. 12)

MGIDYQCGTGHGIGFV (SEQ ID No. 13)

Figure 13:
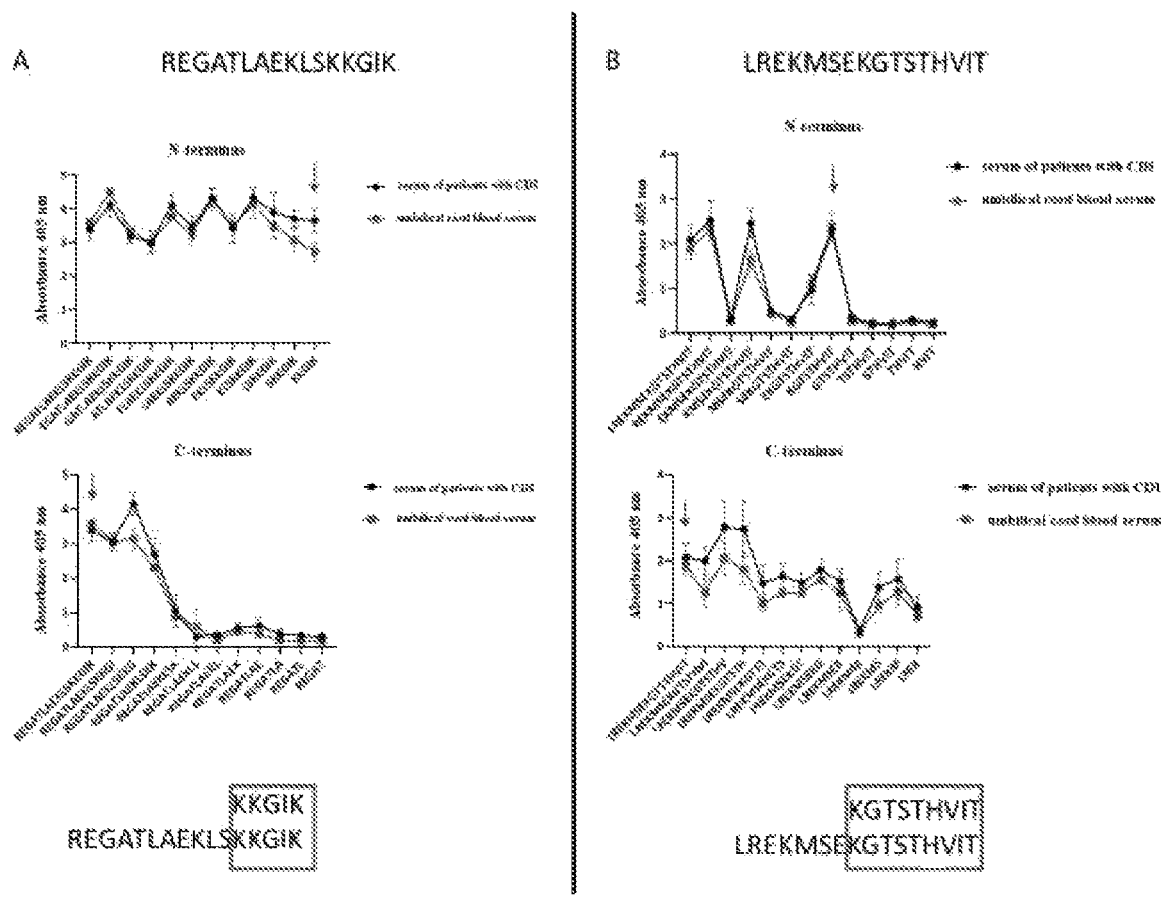
FIG. 13. selecting the shortest immunoreactive sequences (epitopes) of M24 protein. The upper panel shows truncation from N-terminus; the lower panel from C-terminus. 13 A—the truncation of REGATLAEKLSKKGIK peptide (SEQ ID NO:11); 13B—the truncation of LREKMSEKGTSTHVIT peptide (SEQ ID NO:12).

Subsequently, analysis based on determining a minimal epitope was carried out (the shortest immunoreactive sequences) (FIG. 13). The following epitopes were identified in M24 protein:

131KKGIK135 (SEQ ID No. 14)

184KGTSTHVIT192 (SEQ ID No. 15)

In order to study the properties of a vaccine composed of nanoadjuvant and epitope conjugates with a carrier protein, animal testing was carried out:

Example 11—Animal Testing—Adjusting Conjugate Concentration

For this experiment, 6-8 weeks old mice C57BL/6 were used (n=5 per group). The immunogenicity of epitope conjugates with KLH carrier protein was analysed. Epitope sequences: K2 ATGKKGSETPTGKTKV (SEQ ID NO: 16), K3 VNKIKNRPYYKGNIPG (SEQ ID NO: 23), K4 KKGIK (SEQ ID NO: 14). Conjugates were mixed with a well-researched adjuvant, alum, and such a vaccine was administered subcutaneously. The immunogenicity of individual conjugates K2, K3 or K4, as well as their mixtures in one formulation were analysed (Table 4). Mice were vaccinated twice 4 weeks apart. Blood samples (200-400 µl) were collected every 14 days for the duration of the experiment in order to obtain serum to assay the level of IgG, IgA, IgM antibodies and to assay the level of conjugate-specific antibodies in the ELISA test.

TABLE 4

| Conjugate dose selection experiment, description of groups | | | | | |
|---|---|---|---|---|---|
| Group | Formulation | Adjuvant | Dosage [ug] | Administration | Number of mice in the group |
| 1 | conjugate 2 + alum | alum | 10 | subcutaneously | 5 |
| 2 | conjugate 2 + alum | alum | 20 | subcutaneously | 5 |
| 3 | conjugate 3 + alum | alum | 10 | subcutaneously | 5 |
| 4 | conjugate 3 + alum | alum | 20 | subcutaneously | 5 |
| 5 | conjugate 4 + alum | alum | 10 | subcutaneously | 5 |
| 6 | conjugate 4 + alum | alum | 20 | subcutaneously | 5 |
| 7 | conjugate (2, 3, 4) + alum | alum | 3 × 10 | subcutaneously | 5 |
| 8 | conjugate (2, 3, 4) + alum | alum | 3 × 20 | subcutaneously | 5 |
| 9 | alum | alum | 0 | subcutaneously | 5 |
| 10 | PBS | alum | 0 | subcutaneously | 5 |

Figure 14:
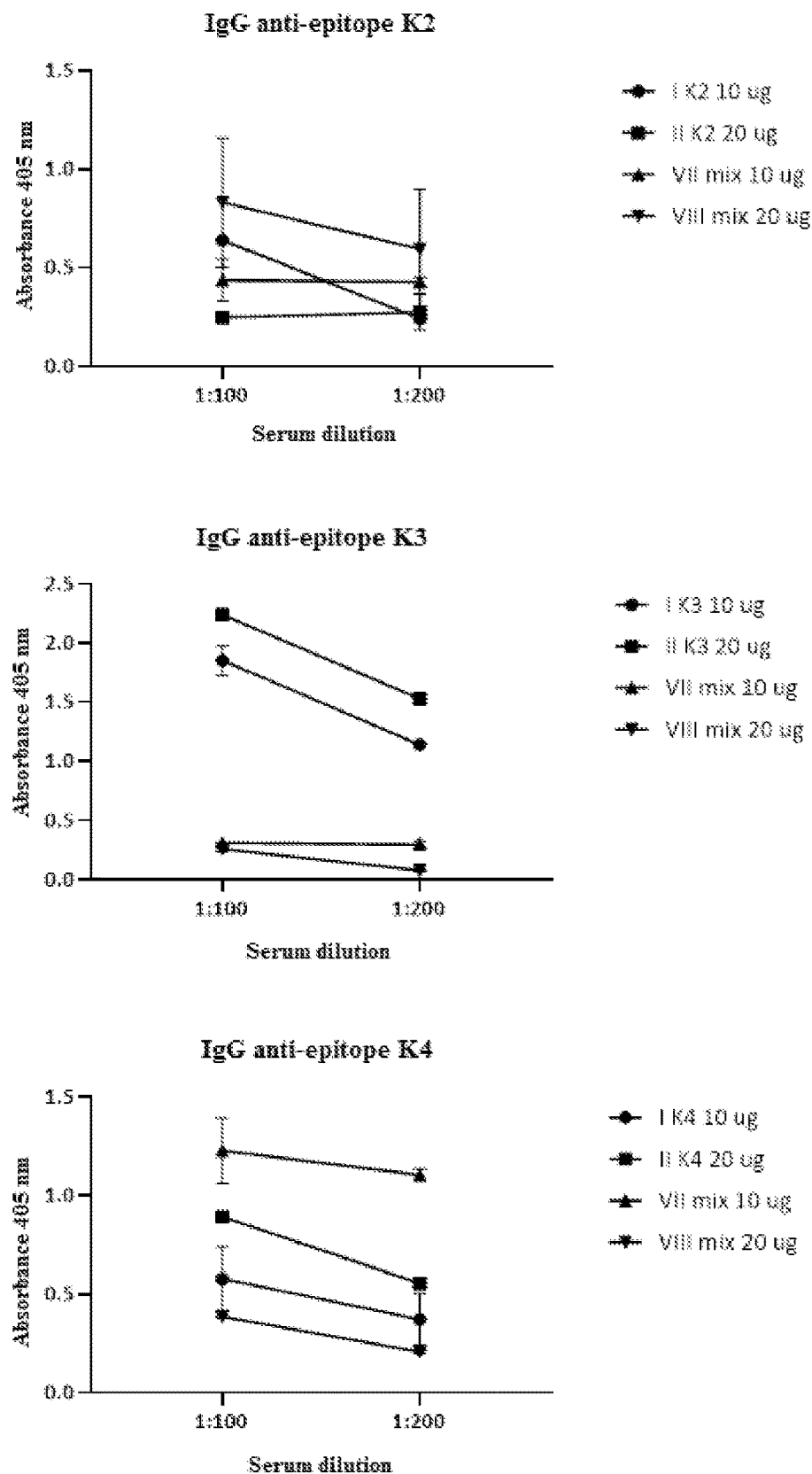
FIG. 14. The result of conjugate immunogenicity testing together with the model adjuvant for intraperitoneal administration. The result is shown for individual epitopes.

Results of assays of specific antibodies show that conjugates are immunogenic (FIG. 14) and a specific response to K2, K3 and K4 epitopes in the form of IgG antibodies was obtained. In the case of K4, a surprising additive effect was observed. Administering this conjugate together with the others enhances the response to it.

Example 12—Immunogenicity of the Vaccine

As the conducted studies on tolerance have shown, nanoadjuvant concentration equal to 10% is safe for intranasal administration to mice. Nanoadjuvant concentration equal to 2.5% is safe for intramuscular administration. Those concentrations were used in the study of immunogenicity of conjugates together with the nanoadjuvant. The immunogenicity of a formulation consisting of the set of conjugates described in Example 11 was analysed, namely K2 ATGKKGSETPTGKTKV (SEQ ID NO: 16), K3 VNKIKNRPYYKGNIPG (SEQ ID NO: 23), K4 KKGIK (SEQ ID NO: 14) as mixtures in concentrations of 7 µg/mouse for every conjugate. Individual groups were described in Table 5. During the experiment, blood was sampled in order to assay general IgG, IgA antibodies and specific antibodies against IgG, IgA conjugates in blood serum of vaccinated mice.

TABLE 5

Study of formulation immunogenicity. Description of groups

| Group No. | Description | Number of mice | Nanoadjuvant concentration | Route of administration |
|---|---|---|---|---|
| 1 | 1-ac-tyl-03 + mix | 5 | 10% | intranasally |
| 2 | 1-et-tyl-02 + mix | 5 | 10% | intranasally |
| 3 | 1-et-tyl-03 + mix | 5 | 10% | intranasally |
| 4 | PBS | 5 | 0% | intranasally |
| 5 | 1-ac-tyl-03 + mix | 5 | 2.5% | intramuscular |
| 6 | 1-et-tyl-02 + mix | 5 | 2.5% | intramuscular |
| 7 | alum + mix | 5 | 0% | intramuscular |
| 8 | PBS | 5 | 0% | intramuscular |

Figure 15:
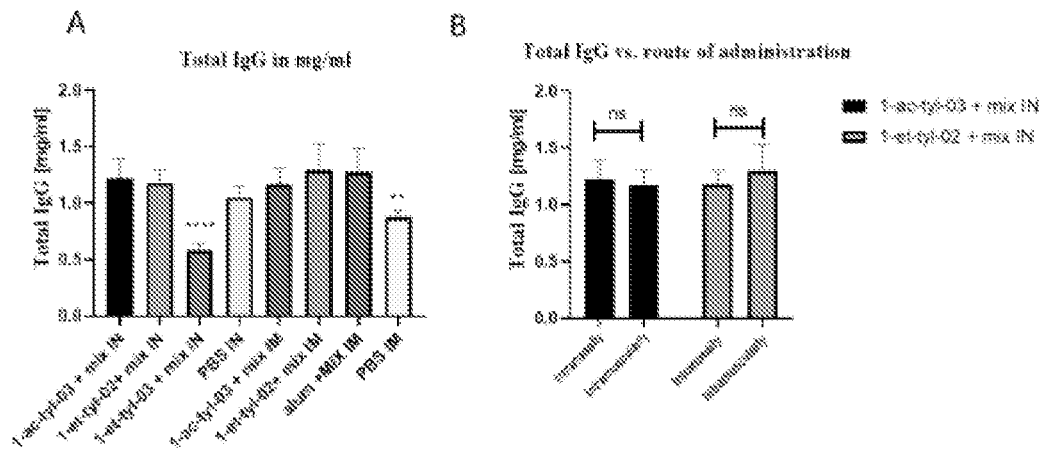
FIG. 15. Total IgG antibodies. 15A—the amount of induced IgG antibodies; 15B—the comparison between the number of total IgG antibodies and the route of administration of the formulation.

The level of total IgG antibodies created as a result of administering the formulation (the nanoadjuvant+a set of conjugates) intranasally is comparable to the level of total IgG antibodies obtained after the intramuscular administration of the same set of conjugates in a vaccine with alum (FIGS. 15A and 15B). This means that nanoadjuvant administered intranasally shows similar adjuvant characteristics as alum, considering the level of total IgG antibodies.

Figure 16:
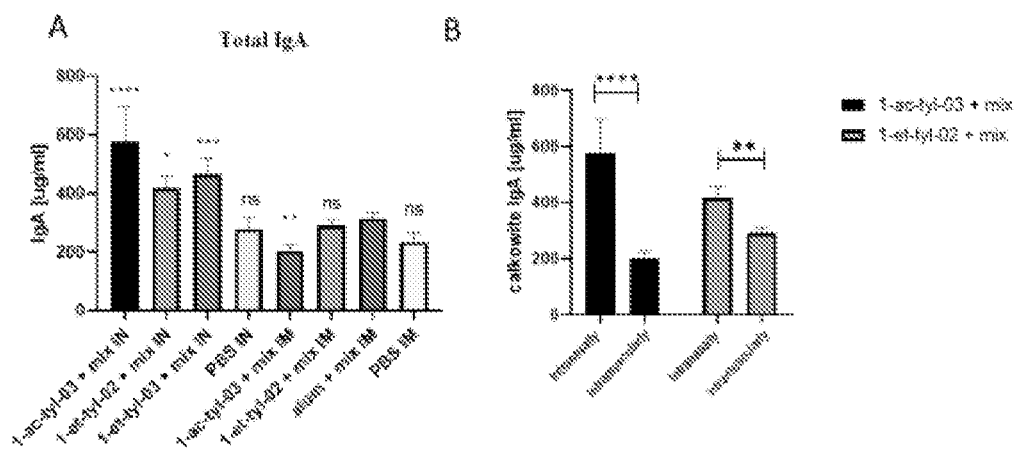
FIG. 16. Total IgA antibodies. 16A—the amount of induced IgA antibodies; 16B—the comparison between the number of total IgA antibodies and the route of administration of the formulation.

The level of total IgA antibodies created as a result of administering the formulation (the nanoadjuvant+a set of conjugates) intranasally is statistically significantly higher than the level of IgA antibodies obtained after the intramuscular administration of the same set of conjugates in a vaccine with alum (FIG. 16A). It means that the nanoadjuvant in a formulation with conjugates stimulates the mucosal response in a much stronger way than the model adjuvant alum, which is a non-obvious observation.

Figure 17:
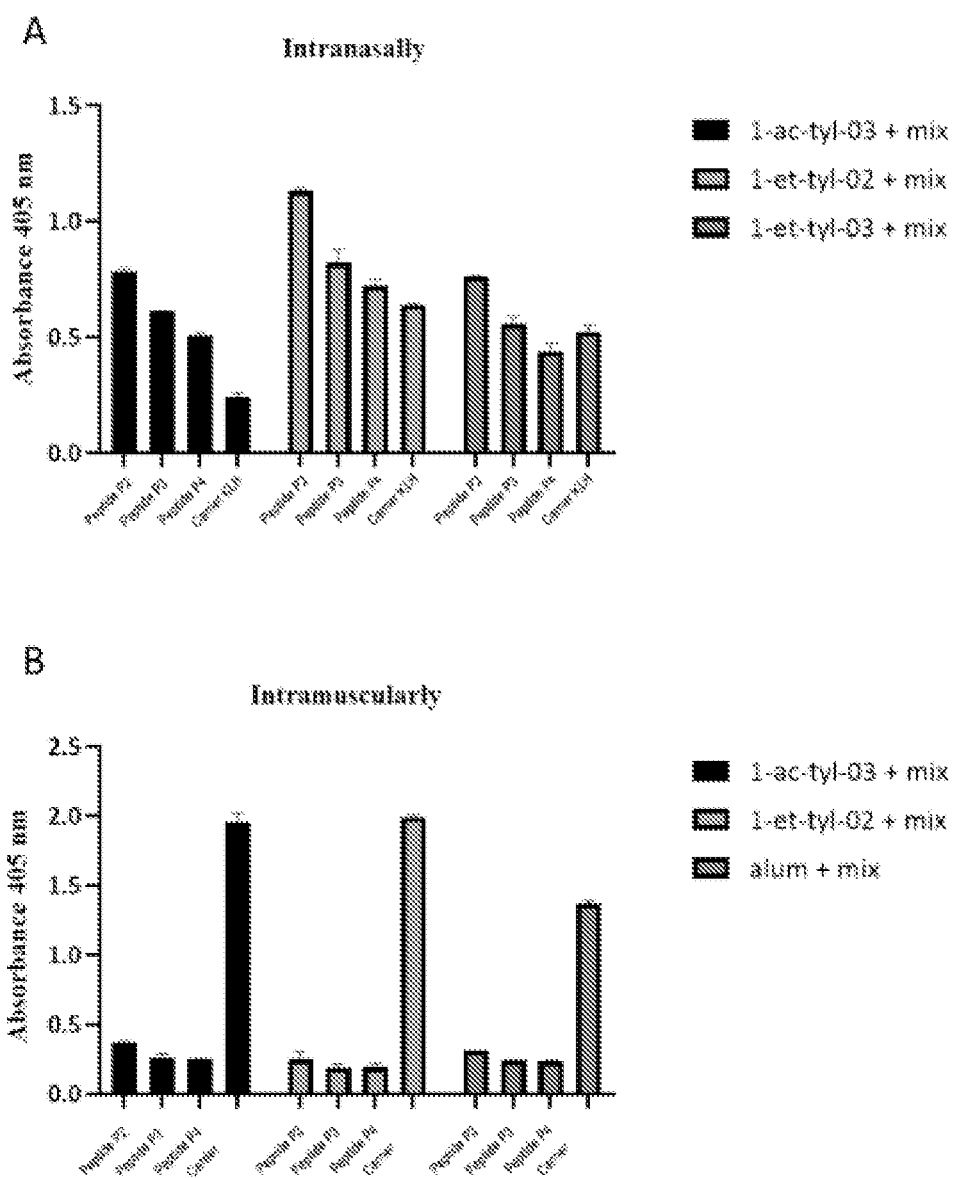
FIG. 17. A comparison of the epitope-specific response. 17A—a comparison of the epitope-specific response for intranasal administration of the formulation; 17B—a comparison of the epitope-specific response for intramuscular administration of the formulation.

A specific response for conjugates provided in formulation was analysed (FIG. 17). As a result of intranasal vaccination, a specific response against given conjugates was obtained with a low level of specific antibodies directed against the carrier, which is a non-obvious observation (FIG. 17A). In the case of intramuscular vaccination, a high level of specific antibodies directed against carrier and low against individual antigens is observed, which is also a non-obvious result (FIG. 17B). Is it a non-obvious property of nanoadjuvants—when combined with a conjugate and administered intranasally, they induce a specific response for an epitope.

Example 13—Protective Tests

C57BL/6 mice were treated with antibiotics in order to sensitise them to a *Clostridium difficile* infection (CD) according to the scheme described above [12]. 8 weeks prior to the antibiotic therapy, mice were immunized with a formulation consisting of the nanoadjuvant and conjugate comprising peptide and carrier protein and faecal samples were collected in order to rule out being CD-positive. 4 weeks later, the immunisation was repeated and another 4 weeks later, an antibiotic therapy lasting 3 days took place. Subsequently, mice were inoculated orally with *C. difficile* (105 CFU). As a control, unimmunized mice (with PBS administered), mice immunized only with the conjugate and mice immunized with the conjugate with MPL were used. Mice were observed for symptoms of infection (weight loss, diarrhoea, mortality). 3 days after the bacteria were administered, faecal samples were collected in order to verify the presence of *C. difficile* and toxins produced by this bacteria. Mice were observed up to 6 days after administering bacteria, and then blood was sampled in order to determine the titer of specific antibodies (ELISA).

Example 14

A 5-months old hen was immunized with a formulation of the invention consisting of 200 µl of the nanoadjuvant of 1% concentration comprising 0.1 mg of epitope conjugate with a carrier protein, 0.1 mg toxins A and B of *Clostridium difficile*, 0.05 mg MPL. Injection was made into neck fold and after two weeks the vaccination was repeated. IgY antibodies were isolated from eggs collected a week after the second injection.

Using the nanoadjuvant with specific antigens as a vaccine against *Clostridium difficile* to obtain therapeutic antibodies is an entirely new, non-obvious solution and has numerous advantages. Nanoadjuvants are prepared in a very easy way in terms of techniques, and the whole procedure is easy to adapt for the use on an industrial scale. In the manufacturing of nanoadjuvants, commonly known compounds are used, such as synthetic oil (e.g. dimethylpolysiloxane), cationic detergents widely used industrially and organic compounds. All used compounds are on a so-called GRAS (Generally Recognized As Safe) list.

Nanoadjuvants are very stable under cooling conditions and even at room temperature, and in the case of short-term storage, they do not require storing in a refrigerator. Storing in a refrigerator up to one year does not show effects typical for emulsion ageing, namely creaming, sedimentation, flocculation, phase inversion, or coalescence. They do not change their physicochemical properties for at least 12 month of storage under cooling conditions. Nanoadjuvants interact with an antigen which spontaneously reaches the inside of drops right after its addition, which has been observed in the form of the increase of drop sizes and decrease in the zeta potential. Nanoadjuvants load protein antigen efficiently, retaining them inside and therefore act perfectly as a carrier of a potential vaccine and act as an adjuvant using the so-called depot effect. The protein antigen closed in a lipid encapsulation is separated from harmful environmental conditions, such as oxidating agents, as well as proteases. Consequently, an intact structure is maintained for a long time.

The surface of mucosa is coated by a layer of protective mucus, in which negatively charged mucin is present apart from enzymes and other proteins. Electrostatic binding to mucin is an effective way of increasing bioadhesion of the vaccine carrier. Nanoadjuvants being a component of the vaccine of the invention bind to mucin, which has been analysed using Zetasizer Nano ZS. Binding depends on the content of the nanoadjuvant and potential zeta resulting from it.

It is a condition of effective immunisation to induce the so-called danger signals, which are usually created during bacterial infection or in a process of eukaryotic cell death [13]. It is therefore preferred that the vaccine carrier acts to some extent in a cytotoxic and proinflammatory way. Nanoadjuvants with low concentrations and short periods of contact are not cytotoxic and by increasing their concentration it is possible to adjust the cytotoxicity level depending on needs. Moreover, nanoadjuvants show proinflammatory activity. When administered together with an antigen, they induce the secretion of TNFα by macrophages. They are not immunogenic by themselves. Nanoadjuvants also induce the antigen uptake by antigen-presenting cells and influence its presentation by increasing the protein expression responsible for that, namely MHC class II proteins. In animal testing, nanoadjuvants increase the titer of specific antibodies in serum of immunized animals, especially for intranasal administration. They can be administered intramucosally and do not exhibit toxic activity even in high concentrations, e.g. 20%.

It should be highlighted that nanoadjuvants are very suitable for intramucosal, especially intranasal, administration. Their advantage lies not only in interaction with mucin present in the mucosa but also in induction of absorption of the delivered antigen by respiratory epithelial cells. It was presented not only by using whole *Clostridium difficile* but also DQ-OVA. Furthermore, mice vaccinated intranasally with formulation consisting of the conjugate and nanoadjuvant showed an increased production of total IgA antibodies and epitope-specific antibodies IgG. Surprisingly, for intranasal administration, the nanoadjuvant significantly enhances the epitope response with simultaneous decrease of the carrier protein response. The example of intramuscular vaccine using commonly used alum presented above shows that the strong response to carrier protein can be a very big problem.

Nanoadjuvant in conjunction with *Clostridium difficile* antigens in the form of epitope conjugates with carrier protein, A and B toxins and additional immunostimulats allow for obtaining a high titer and a large amount of specific therapeutic antibodies in a relatively short time. Such antibodies used in humans as auxiliary means during infection or for its prevention act on the early stage of the infection and protect the mucous membrane of bowels by neutralizing the effect of toxins.

Basing on the above embodiments, the preferred composition of vaccine formulation is a 10% solution of one of nanoadjuvants: 1-et-tyl-03, 1-ac-tyl-03, 1-et-t80-03, 1-et-tyl-05, 1-et-t80-05 and 1-et-tyl-02 with suspended CD antigens in the form of epitope conjugates with a carrier protein (in a concentration of 10 μg for a mouse, 100 μg for a hen). Amino acid sequences of 71 kDa protein epitopes: ATGKKGSETPTGKTKV (SEQ ID NO: 16), VNKIKNRPYYKGNIPG (SEQ ID NO: 23), SRKNTLGYFVNNKLVK (SEQ ID NO: 24), GTYOKNSWLKVNGKMY (SEQ ID NO: 7), QTGWQEKNGKKYYLGS (SEQ ID NO: 6), TGWKTENGKKYYVKSD SEQ ID NO: 17), NKKYYLGTDGARVSGW (SEQ ID NO: 18), FDTAKKISSVGNWNAD (SEQ ID NO: 19), EFRVAT (SEQ ID NO: 8), KVNGKM (SEQ ID NO: 9) and WQEKNGKKYY (SEQ ID NO: 10) and M24 proteins: FISGFNGSAGTVIVTK (SEQ ID NO: 20), REGATLAEKKLSKKGIK (SEQ ID NO: 21), KKGIKIEYQYDLIDGI (SEQ ID NO: 22), LREKMSEKGTSTHVIT (SEQ ID NO: 12), MGIDYQCGTGHGIGFV (SEQ ID NO: 13), KKGIK (SEQ ID NO: 14) and KGTSTHVIT (SEQ ID NO: 15). Inactivated toxins TcdA and TcdB of *Clostridium difficile* (1 μg for mouse, 10 μg for hen) can be added to the formulation, as well as other immunomodulating agents, including probiotic bacteria antigens of *Lactobacillus, Bifidobacterium, Akkermansia* or *Faecalibacterium* species such as: polysaccharides, teichoic acids, lipoteichoic acids, proteins, peptidoglycans, glycolipids, lipopolysaccharides, monophosphorylic lipid A, glycoproteins, bacteriocins, DNA, RNA, enzymes, peptides and other particles secreted to the medium. Other immunomodulating components not derived from bacteria, including cytokines and modifications thereof, nonimmunogenic peptides, lipids, polar proteins.

The use of formulation for vaccinating hens in order to obtain therapeutic antibodies is one of the uses of the invention. Manufacturing of IgY-class antibodies is used on an industrial scale. To produce IgY antibodies, a very small dose, as much as micrograms of antigen is needed, and a high titer of antibodies is maintained from a few weeks to a few months. During that time, a high amount of protective IgY antibodies is transferred to an egg. The use of IgY has many advantages: (1) IgY do not react with human complement system, therefore the non-specific inflammatory reaction can be avoided, (2) during the manufacturing, no toxic compounds were used, neither for vaccination nor in the time of cleaning the IgY antibodies, (3) in a method that is very easy to scale, as we are able to discard from the formulation all components apart from IgY. The use of passive immunization in the form of IgY formulation has a range of additional advantages: the activity is virtually immediate and focused on a specific area, namely the digestive system, it is highly specific, it can be used in humans of all ages and those with immunodeficiencies, it is entirely non-toxic because it includes components, which are normally present in our diet.

Owing to the production technology used, it is very easy to manipulate the composition of the formulation for vaccinating hens in order to obtain antibodies adjusted for changing strains, should they develop resistance. It would be possible to use another epitope from a group of already described epitopes. The obtained product will be administered orally in the form of a water-soluble powder. A novel formulation for the delivery of unchanged IgY antibodies to bowels of the patient where it will act therapeutically will be developed. As a result, it is possible to decrease the dosage.

REFERENCES

1. Adjonu, R., Doran, G., Torley, P. and Agboola, S. 2014. Whey protein peptides as components of nanoemulsions: A review of emulsifying and biological functionalities. Journal of Food Engineering. 122, (February 2014), 15-27.
2. Bielinska, A. U., Gerber, M., Blanco, L. P., Makidon, P. E., Janczak, K. W., Beer, M., Swanson, B. and Baker, Jr., J. R. 2010. Induction of Th17 Cellular Immunity With a Novel Nanoemulsion Adjuvant. Critical Reviews™ in Immunology. 30, 2 (2010), 189-199.
3. Bielinska, A. U., Janczak, K. W., Landers, J. J., Markovitz, D. M., Montefiori, D. C. and Baker, J. R. 2008. Nasal immunization with a recombinant HIV gp120 and nanoemulsion adjuvant produces Th1 polarized responses and neutralizing antibodies to primary HIV type 1 isolates. AIDS research and human retroviruses. 24, 2 (February 2008), 271-281.
4. Bielinska, A. U., Makidon, P. E., Janczak, K. W., Blanco, L. P., Swanson, B., Smith, D. M., Pham, T., Szabo, Z., Kukowska-Latallo, J. F. and Baker, J. R. 2014. Distinct Pathways of Humoral and Cellular Immunity Induced with the Mucosal Administration of a Nanoemulsion Adjuvant. The Journal of Immunology. 192, 6 (March 2014), 2722-2733.
5. Makidon, P. E., Bielinska, A. U., Nigavekar, S. S., Janczak, K. W., Knowlton, J., Scott, A. J., Mank, N., Cao, Z., Rathinavelu, S., Beer, M. R., Wilkinson, J. E., Blanco, L. P., Landers, J. J. and Baker, J. R. 2008. Pre-Clinical Evaluation of a Novel Nanoemulsion-Based Hepatitis B Mucosal Vaccine. PLoS ONE. 3, 8 (August 2008), e2954.
6. Wong, P. T. et al. 2015. Formulation, High Throughput In Vitro Screening and In Vivo Functional Characterization of Nanoemulsion-Based Intranasal Vaccine Adjuvants. PLoS ONE. 11, (2015).
7. Pechine et al. 2018. Targeting *Clostridium difficile* surface components to develop immunotherapeutic strategies against *Clostridium difficile* infection 8. Rodriguez-Palacios A, Borgmann S, Kline T R et al (2013) *Clostridium difficile* in foods and animals: history and measures to reduce exposure. Anim Health Res Rev 14:11-29
9. Elixhauser, A. and Jhung, M. *Clostridium difficile* Diseases in US Hospitals; AHRQ, Centre for Delivery, Organization and Markets, Healthcare Cost and Utilization Project. 2008.
10. Lai, K. K., Melvin, Z. S., Menard, M. J., Kotilainen, H. R., and Baker, S. *Clostridium difficile* associated diarrhea: epidemiology, risk factors, and infection control. Infect. Control. Hosp. Epidemiol., 18 (1997), 628-632.
11. Pepin, J., Routhier, S., Gagnon, S., and Brazeau, I. Management and outcomes of a first recurrence of *Clostridium difficile*-associated disease in Quebec, Canada. Clin. Infect. Dis., 42 (2006), 758-764.
12. Hryniewicz W., Martirosian G., Ozorowski T.: Zakażenia *Clostridium difficile*. Diagnostyka, terapia, profilaktyka. Narodowy Program Ochrony Antybiotyków. Ministerstwo Zdrowia, Warszawa 2011, http://www.antybiotyki.edu.pl/pdf/*Clostridium difficile* v6_10.pdf.

The invention claimed is:

1. A vaccine comprising conjugates of epitopes of surface proteins 71 kDa of SEQ ID No. 1 and aminopeptidase M24 of SEQ ID No. 2 from *Clostridium difficile* suspended in emulsion, comprising additional immunostimulating components and *Clostridium difficile* toxins.

2. The vaccine according to claim 1, wherein a synthetic oil is a component of the emulsion.

3. The vaccine according to claim 1, wherein the 71 kDa protein epitope has the amino acid sequence defined in SEQ ID No. 8, 9 and 10.

4. The vaccine according to claim 1, wherein the M24 protein epitope has the amino acid sequence defined in SEQ ID No. 14 and 15.

5. The vaccine according to claim 1, wherein the epitopes are selected from K2 ATGKKGSETPTGKTKV (SEQ ID. No. 16), K3 VNKIKNRPYYKGNIPG (SEQ ID. No. 23) and K4 KKGIK (SEQ ID. No. 14).

6. The vaccine according to claim 1, wherein the *Clostridium difficile* toxins are the TcdA and TcdB toxin or their inactivated versions.

7. The vaccine according to claim 1, wherein, apart from synthetic oil, the emulsion comprises an organic solvent, a non-ionic detergent, a cationic detergent and ultrapure water.

8. The vaccine according to claim 2, wherein the synthetic oil is dimethylpolysiloxane.

9. The vaccine according to claim 7, wherein the organic solvent is selected from ethanol or acetone.

10. The vaccine according to claim 7, wherein the non-ionic detergent is tyloxapol.

11. The vaccine according to claim 7, wherein the emulsion is 1-et-tyl-03, 1-ac-tyl-03, or 1-et-tyl-02, wherein the components of nanoadjuvant in the form of emulsion are combined in the ratio of 60-70% oil, 4-8% non-ionic detergent, 1-3% cationic detergent, 5-10% organic solvent, and 15-25% ultrapure water.

12. The vaccine according to claim 11, wherein 1-et-tyl-03 is a combination of 65% dimethylpolysiloxane, 5% tyloxapol, 1% benzyldimethyldodecylammonium chloride, 8% ethanol and 21% water; 1-ac-tyl-03 is 65% dimethylpolysiloxane, 5% tyloxapol, 1% benzyldimethyldodecylammonium chloride, 8% acetone and 21% water; and 1-et-tyl-02 is 65% dimethylpolysiloxane, 5% tyloxapol, 1% cetylpyridinium bromide, 8% ethanol and 21% water.

13. The vaccine according to claim 1, wherein the immunostimulating components are antigens of probiotic bacteria comprising polysaccharides, teichoic acids, lipoteichoic acids, proteins, peptidoglycan, glycolipids, lipopolysaccharides, monophosphorylic lipid A, glycoproteins, bacteriocins, DNA, RNA, enzymes, and/or peptides secreted to the medium.

14. The vaccine according to claim 1, wherein the vaccine is administered parenterally and/or intramucosally.

15. A method for treating *C. difficile* infections in animals, the method comprising administering the vaccine of claim 1 to said animals.

16. The method of claim 15, wherein the treated animals are birds and mammals.

17. A method for production of a *C. difficile*-specific antibody, the method comprising administering the vaccine of claim 1 to an animal.

18. The method of claim 17, wherein the *C. difficile*-specific antibody is an IgY antibody and wherein the vaccine is administered intramuscularly to birds, optionally to chickens.

19. The vaccine according to claim 1, wherein the vaccine is administered intranasally.

* * * * *

SEQUENCE LISTING

```
<160> NUMBER OF SEQ ID NOS: 24

<210> SEQ ID NO 1
<211> LENGTH: 642
<212> TYPE: PRT
<213> ORGANISM: Clostridium difficile

<400> SEQUENCE: 1

Met Lys Lys Ser Leu Lys Lys Tyr Leu Val Leu Ala Leu Thr Leu Val
1               5                   10                  15

Leu Val Phe Ala Cys Gly Val Pro Glu Ser Ser Ala Ala Ser Lys His
                20                  25                  30

Val Ile Ile Val Asn Ser Arg Lys Asn Thr Leu Gly Tyr Phe Val Asn
            35                  40                  45

Asn Lys Leu Val Lys Glu Phe Arg Val Ala Thr Gly Lys Lys Gly Ser
        50                  55                  60

Glu Thr Pro Thr Gly Lys Thr Lys Val Asn Lys Ile Lys Asn Arg Pro
65                  70                  75                  80

Tyr Tyr Lys Gly Asn Ile Pro Gly Gly Ser Pro Arg Asn Pro Leu Gly
                85                  90                  95

Asp Arg Trp Met Gly Leu Ala Leu Lys Gly Thr Tyr Gly Asp Thr Tyr
                100                 105                 110

Gly Ile His Gly Asn Asn Asn Glu Ser Ser Ile Gly Lys His Ile Ser
            115                 120                 125

Gly Gly Cys Ile Arg Met His Asn Lys Asp Val Trp Leu Phe Asp Gln
        130                 135                 140

Val Pro Val Gly Ser Asp Val Ile Ile Asp Tyr Ser Asn Asp Ser Tyr
145                 150                 155                 160

Val Lys Ile Ala Ala Lys Tyr Lys Ile Asn Leu Asn Gln Thr Gly Trp
                165                 170                 175

Lys Thr Glu Asn Gly Lys Lys Tyr Tyr Val Lys Ser Asp Gly Thr Tyr
                180                 185                 190

Gln Lys Asn Ser Trp Leu Lys Val Asn Gly Lys Met Tyr Tyr Phe Asp
            195                 200                 205

Ala Ser Gly Val Met Gln Thr Gly Trp Lys Ala Ile Asn Asn Lys Lys
        210                 215                 220

Tyr Tyr Leu Gly Thr Asp Gly Ala Arg Val Ser Gly Trp Lys Val Ile
225                 230                 235                 240

Asp Gly Lys Thr Tyr Tyr Phe Asn Ser Asp Gly Val Met Gln Thr Gly
                245                 250                 255

Trp Gln Glu Lys Asn Gly Lys Lys Tyr Tyr Leu Gly Ser Asp Gly Leu
            260                 265                 270

Ser Val Thr Gly Trp Gln Glu Ile Asp Gly Asn Lys Tyr Tyr Phe Asp
        275                 280                 285

Lys Thr Gly Ile Met Gln Thr Gly Trp Gln Gln Ile Asp Gly Lys Ser
```

```
                    290                 295                 300
Tyr Tyr Leu Asp Lys Asp Gly Lys Met Leu Thr Gly Ser Gln Lys Ile
305                 310                 315                 320

Asp Gly Lys Asp Tyr Thr Phe Asn Glu Asp Gly Thr Ile Asn Pro Thr
                325                 330                 335

Trp Asp Thr Ile Ile Gly Ala Asn Arg Phe Asp Thr Ala Lys Lys Ile
            340                 345                 350

Ser Ser Val Gly Asn Trp Asn Ala Asp Ser Ser Asp Thr Val Ile Leu
        355                 360                 365

Val Asn Gly Asn Ala Ile Ala Asp Gly Ile Thr Ala Thr Pro Leu Ala
    370                 375                 380

Ser Ser Tyr Asp Ser Thr Ile Leu Leu Thr Asn Thr Ala Asn Leu Pro
385                 390                 395                 400

Thr Glu Thr Val Glu Glu Met Lys Leu Leu Ala Pro Lys Thr Val Ile
                405                 410                 415

Leu Ile Gly Gly Glu Asn Ala Ile Ser Ser Lys Leu Glu Gln Glu Ile
            420                 425                 430

Lys Thr Thr Phe Asn Thr Glu Thr Lys Arg Ile Ala Gly Gln Asp Arg
        435                 440                 445

Tyr Gln Thr Ala Thr Arg Ile Ala Glu Glu Leu Gly Asn Arg Glu Glu
    450                 455                 460

Ile Lys Thr Ala Tyr Met Val Ser Gly Asn Gly Glu Ala Asp Ala Leu
465                 470                 475                 480

Ser Val Ala Ser Lys Ala Gly Glu Glu Lys Gln Pro Ile Ile Leu Val
                485                 490                 495

Asn Lys Asp Gly Ile Thr Glu Glu Ser Tyr Lys Trp Leu Thr Glu Arg
            500                 505                 510

Lys Leu Glu Asn Ala Tyr Phe Ile Gly Gly Pro Ser Ala Ile Asn Asp
        515                 520                 525

Ser Val Ile Ala Lys Met Asn Asp Ile Thr Thr Glu Asp Ile Ser Gly
    530                 535                 540

Asn Arg Ile Tyr Gly Asp Ser Arg Val Asp Thr Asn Ala Lys Val Ile
545                 550                 555                 560

Glu Lys Phe Tyr Gly Asp Thr Asp Leu Gln Ala Val Leu Val Ser Lys
                565                 570                 575

Ser Asp Ala Leu Val Asp Ala Leu Ser Ala Gly Pro Leu Ala Val Lys
            580                 585                 590

Leu His Ser Pro Ile Val Leu Met Asp Asn Ser Gly Leu Ser Leu Glu
        595                 600                 605

Gln Gln Arg Val Phe Ala Asn Lys Lys Val Glu Thr Pro Tyr Gln Ile
    610                 615                 620

Gly Gly Gly Val Ser Tyr Ile Val Met Asp Lys Leu Met Asp Ile Leu
625                 630                 635                 640

Ala Lys

<210> SEQ ID NO 2
<211> LENGTH: 597
<212> TYPE: PRT
<213> ORGANISM: Clostridium difficile

<400> SEQUENCE: 2

Met Asn Ile Lys Asp Arg Leu Ser Gly Leu Arg Lys Phe Met Glu Glu
1               5                   10                  15

Lys Asn Ile Asp Ala Tyr Met Ile Pro Ser Ser Asp Asn His Gln Ser
```

-continued

```
             20                  25                  30
Glu Tyr Val Gly Asp Tyr Phe Lys Ser Arg Glu Phe Ile Ser Gly Phe
         35                  40                  45

Asn Gly Ser Ala Gly Thr Val Ile Val Thr Lys Asp Glu Ala Gly Leu
     50                  55                  60

Trp Thr Asp Gly Arg Tyr Phe Ile Gln Ala Glu Ser Gln Leu Glu Gly
 65                  70                  75                  80

Ser Thr Ile Lys Leu Phe Lys Met Gly Gln Glu Gly Cys Pro Thr Thr
                 85                  90                  95

Asp Glu Tyr Leu Tyr Lys Asn Ile Pro Glu Gly Gly Thr Leu Gly Phe
             100                 105                 110

Asp Gly Arg Val Ile Ser Ala Arg Glu Gly Ala Thr Leu Ala Glu Lys
         115                 120                 125

Leu Ser Lys Lys Gly Ile Lys Ile Glu Tyr Gln Tyr Asp Leu Ile Asp
     130                 135                 140

Gly Ile Trp Pro Asp Arg Pro Ala Leu Ser Asp Ser Lys Ala Phe Leu
145                 150                 155                 160

Leu Asp Val Lys Tyr Cys Gly Glu Ser Phe Ser Ser Lys Leu Ala Arg
                 165                 170                 175

Leu Arg Glu Lys Met Ser Glu Lys Gly Thr Ser Thr His Val Ile Thr
             180                 185                 190

Thr Leu Asp Asp Ile Ala Trp Leu Phe Asn Ile Arg Gly Gly Asp Val
         195                 200                 205

Lys Tyr Asn Pro Val Val Leu Ser Tyr Ala Val Ile Thr Leu Lys Glu
     210                 215                 220

Val Tyr Leu Phe Val Asp Glu Ser Lys Leu Asn Glu Glu Ile Leu Asp
225                 230                 235                 240

Glu Leu Ala Lys Glu Asn Val Gln Ile Lys Pro Tyr Asn Asp Val Tyr
                 245                 250                 255

Glu Phe Val Lys Asn Ile Asp Lys Thr Glu Lys Val Leu Leu Asp Gly
             260                 265                 270

Thr Lys Leu Ser Tyr Thr Ile Tyr Asn Asn Ile Pro Cys Glu Val Glu
         275                 280                 285

Lys Val Asp Glu Phe Asn Pro Val Met Phe Phe Lys Ala Gln Lys Asn
     290                 295                 300

Glu Val Glu Leu Glu Asn Ile Arg Asn Ser His Val Lys Asp Gly Val
305                 310                 315                 320

Ala Phe Thr Lys Phe Met Tyr Trp Leu Lys Lys Asn Val Gly Lys Met
                 325                 330                 335

Glu Ile Thr Glu Ile Ser Ala Thr Gln Lys Leu Glu Asp Leu Arg Arg
             340                 345                 350

Glu Gln Glu Gly Phe Phe Glu Pro Ser Phe Asn Thr Ile Ala Ala Tyr
         355                 360                 365

Lys Glu His Ala Ala Met Met His Tyr Ser Ala Thr Pro Glu Ser Asn
     370                 375                 380

Tyr Lys Leu Glu Ala Glu Gly Leu Phe Leu Val Asp Ser Gly Gly Gln
385                 390                 395                 400

Tyr Tyr Asp Gly Thr Thr Asp Ile Thr Arg Thr Thr Val Leu Gly Pro
                 405                 410                 415

Ile Ser Asp Glu Leu Lys Leu His Phe Thr Ser Val Ala Arg Gly Met
             420                 425                 430

Ile Asn Leu Ser Lys Ala Lys Phe Leu His Gly Cys Arg Gly Tyr Asn
         435                 440                 445
```

```
Leu Asp Ile Leu Ser Arg Ser Cys Met Trp Asn Met Gly Ile Asp Tyr
    450                 455                 460

Gln Cys Gly Thr Gly His Gly Ile Gly Phe Val Leu Asn Val His Glu
465                 470                 475                 480

Ala Pro Asn Gly Phe Arg Trp Arg Val Val Pro Glu Arg Phe Asp Ser
            485                 490                 495

Ala Val Leu Glu Glu Gly Met Val Thr Thr Asn Glu Pro Gly Ile Tyr
                500                 505                 510

Ile Glu Gly Ser His Gly Ile Arg Thr Glu Asn Glu Ile Val Val Arg
        515                 520                 525

Lys Ala Glu Lys Asn Phe Tyr Gly Gln Phe Met Glu Phe Glu Val Val
    530                 535                 540

Thr Leu Ala Pro Ile Asp Leu Asp Gly Ile Val Pro Glu Leu Met Asn
545                 550                 555                 560

Lys Asp Glu Lys Asp Tyr Leu Asn Trp Tyr His Lys Leu Val Tyr Asp
            565                 570                 575

Lys Ile Ser Pro Phe Leu Thr Asp Glu Arg Glu Trp Leu Lys Val
                580                 585                 590

Tyr Thr Arg Ala Ile
        595

<210> SEQ ID NO 3
<211> LENGTH: 1926
<212> TYPE: DNA
<213> ORGANISM: Clostridium difficile

<400> SEQUENCE: 3
atgaaaaaaa gtttaaaaaa atatttagtt ttagcattaa cattagttttt agttttttgca      60 tgtggagttc ctgaaagtag tgcagcaagt aaacatgtta atagttaa tagtagaaaaa       120 aatacattag atattttgt taataataaa ttagttaaag aatttagagt tgcaacagga       180 aaaaaggaa gtgaaacacc tacaggaaaa acaaaagtta taaaataaa aatagaccct       240 tattataaag gaaatatacc tggaggaagt cctagaaatc ctttaggaga tagatggatg       300
ggattagcat taaaaggaac atatggagat acatatggaa tacatggaaa taataatgaa       360
agtagtatag aaaacatat aagtggagga tgtataagaa tgcataataa agatgttttgg       420 ttatttgatc aagttcctgt tggaagtgat gttataatag attatagtaa tgatagttat       480
gttaaaatag cagcaaaata taaaataaat ttaaatcaaa caggatggaa aacagaaaat       540
ggaaaaaaat attatgttaa aagtgatgga acatatcaaa aaaatagttg gttaaaagtt       600
aatggaaaaa tgtattattt tgatgcaagt ggagttatgc aaacaggatg gaaagcaata       660
aataataaaa aatattattt aggaacagat ggagcaagag ttagtggatg gaaagttata       720
gatggaaaaa catattattt taatagtgat ggagttatgc aaacaggatg gcaagaaaaa       780
aatggaaaaa aatattattt aggaagtgat ggattaagtg ttacaggatg gcaagaaata       840
gatggaaata aatattattt tgataaaaca ggaataatgc aaacaggatg gcaacaaata       900
gatggaaaaa gttattattt agataaagat ggaaaaatgt taacaggaag tcaaaaaata       960
gatggaaaag attatacatt taatgaagat ggaacaataa atcctacatg ggatacaata      1020
ataggagcaa atagatttga tacagcaaaa aaaataagta gtgttggaaa ttggaatgca      1080
gatagtagtg atacagttat attagttaat ggaaatgcaa tagcagatgg aataacagca      1140
acacctttag caagtagtta tgatagtaca atattattaa caaatacagc aaatttacct      1200
```

| | |
|---|---:|
| acagaaacag ttgaagaaat gaaattatta gcacctaaaa cagttatatt aataggagga | 1260 |
| gaaaatgcaa taagtagtaa attagaacaa gaaataaaaa caacatttaa tacagaaaca | 1320 |
| aaaagaatag caggacaaga tagatatcaa acagcaacaa gaatagcaga agaattagga | 1380 |
| aatagagaag aaataaaaac agcatatatg gttagtggaa atggagaagc agatgcatta | 1440 |
| agtgttgcaa gtaaagcagg agaagaaaaa caacctataa tattagttaa taaagatgga | 1500 |
| ataacagaag aaagttataa atggttaaca gaaagaaaat tagaaaatgc atattttata | 1560 |
| ggaggaccta gtgcaataaa tgatagtgtt atagcaaaaa tgaatgatat aacaacagaa | 1620 |
| gatataagtg gaaatagaat atatggagat agtagagttg atacaaatgc aaaagttata | 1680 |
| gaaaaatttt atggagatac agatttacaa gcagttttag ttagtaaaag tgatgcatta | 1740 |
| gttgatgcat taagtgcagg acctttagca gttaaattac atagtcctat agttttaatg | 1800 |
| gataatagtg gattaagttt agaacaacaa agagttttg caaataaaaa agttgaaaca | 1860 |
| ccttatcaaa taggaggagg agttagttat atagttatgg ataaattaat ggatatatta | 1920 |
| gcaaaa | 1926 |

<210> SEQ ID NO 4
<211> LENGTH: 1791
<212> TYPE: DNA
<213> ORGANISM: Clostridium difficile

<400> SEQUENCE: 4

| | |
|---|---:|
| atgaatataa aagatagatt aagtggatta agaaaattta tggaagaaaa aaatatagat | 60 |
| gcatatatga tacctagtag tgataatcat caaagtgaat atgttggaga ttattttaaa | 120 |
| agtagagaat ttataagtgg atttaatgga agtgcaggaa cagttatagt tacaaaagat | 180 |
| gaagcaggat tatggacaga tggaagatat tttatacaag cagaaagtca attagaagga | 240 |
| agtacaataa aattatttaa aatgggacaa gaaggatgtc ctacaacaga tgaatattta | 300 |
| tataaaaata tacctgaagg aggaacatta ggatttgatg gaagagttat aagtgcaaga | 360 |
| gaaggagcaa cattagcaga aaaattaagt aaaaaaggaa taaaaataga atatcaatat | 420 |
| gatttaatag atggaatatg gcctgataga cctgcattaa gtgatagtaa agcatttta | 480 |
| ttagatgtta atattgtgg agaaagtttt agtagtaaat tagcaagatt aagagaaaaa | 540 |
| atgagtgaaa aaggaacaag tacacatgtt ataacaacat tagatgatat agcatggtta | 600 |
| tttaatataa gaggaggaga tgttaaatat aatcctgttg ttttaagtta tgcagttata | 660 |
| acattaaaag aagtttattt atttgttgat gaaagtaaat taaatgaaga atattagat | 720 |
| gaattagcaa agaaaatgt tcaaataaaa ccttataatg atgtttatga atttgttaaa | 780 |
| aatatagata aaacagaaaa agttttatta gatggaacaa aattaagtta tacaatatat | 840 |
| aataatatac cttgtgaagt tgaaaaagtt gatgaattta tcctgttat gtttttaaa | 900 |
| gcacaaaaaa atgaagttga attagaaaat ataagaaata gtcatgttaa agatggagtt | 960 |
| gcatttacaa aattttatgta ttggttaaaa aaaaatgttg gaaaaatgga ataacagaa | 1020 |
| ataagtgcaa cacaaaaatt agaagattta agaagagaac aagaaggatt ttttgaacct | 1080 |
| agttttaata caatagcagc atataaagaa catgcagcaa tgatgcatta tagtgcaaca | 1140 |
| cctgaaagta attataaatt agaagcagaa ggattatttt tagttgatag tggaggacaa | 1200 |
| tattatgatg gaacaacaga tataacaaga acaacagttt taggacctat aagtgatgaa | 1260 |
| ttaaaattac attttacaag tgttgcaaga ggaatgataa atttaagtaa agcaaaattt | 1320 |
| ttacatggat gtagaggata taatttagat atattaagta gaagttgtat gtggaatatg | 1380 |

```
ggaatagatt atcaatgtgg aacaggacat ggaataggat ttgttttaaa tgttcatgaa    1440
gcacctaatg gatttagatg gagagttgtt cctgaaagat ttgatagtgc agttttagaa    1500
gaaggaatgg ttacaacaaa tgaacctgga atatatatag aaggaagtca tggaataaga    1560
acagaaaatg aaatagttgt tagaaaagca gaaaaaaatt tttatggaca atttatgaaa    1620
tttgaagttg ttacattagc acctatagat ttagatggaa tagttcctga attaatgaat    1680
aaagatgaaa aagattattt aaattggtat cataaaattag tttatgataa aataagtcct    1740
tttttaacag atgaagaaag agaatggtta aaagtttata caagagcaat a             1791
```

<210> SEQ ID NO 5
<211> LENGTH: 19
<212> TYPE: PRT
<213> ORGANISM: Clostridium difficile

<400> SEQUENCE: 5

Asn Asn Lys Leu Val Lys Glu Phe Arg Val Ala Thr Gly Lys Lys Ser
1               5                   10                  15

Glu Thr Pro

<210> SEQ ID NO 6
<211> LENGTH: 16
<212> TYPE: PRT
<213> ORGANISM: Clostridium difficile

<400> SEQUENCE: 6

Gln Thr Gly Trp Gln Glu Lys Asn Gly Lys Lys Tyr Tyr Leu Gly Ser
1               5                   10                  15

<210> SEQ ID NO 7
<211> LENGTH: 16
<212> TYPE: PRT
<213> ORGANISM: Clostridium difficile

<400> SEQUENCE: 7

Gly Thr Tyr Gln Lys Asn Ser Trp Leu Lys Val Asn Gly Lys Met Tyr
1               5                   10                  15

<210> SEQ ID NO 8
<211> LENGTH: 6
<212> TYPE: PRT
<213> ORGANISM: Clostridium difficile

<400> SEQUENCE: 8

Glu Phe Arg Val Ala Thr
1               5

<210> SEQ ID NO 9
<211> LENGTH: 6
<212> TYPE: PRT
<213> ORGANISM: Clostridium difficile

<400> SEQUENCE: 9

Lys Val Asn Gly Lys Met
1               5

<210> SEQ ID NO 10
<211> LENGTH: 10
<212> TYPE: PRT
<213> ORGANISM: Clostridium difficile

<400> SEQUENCE: 10

```
Trp Gln Glu Lys Asn Gly Lys Lys Tyr Tyr
1               5                   10

<210> SEQ ID NO 11
<211> LENGTH: 16
<212> TYPE: PRT
<213> ORGANISM: Clostridium difficile

<400> SEQUENCE: 11

Arg Glu Gly Ala Thr Leu Ala Glu Lys Leu Ser Lys Lys Gly Ile Lys
1               5                   10                  15

<210> SEQ ID NO 12
<211> LENGTH: 16
<212> TYPE: PRT
<213> ORGANISM: Clostridium difficile

<400> SEQUENCE: 12

Leu Arg Glu Lys Met Ser Glu Lys Gly Thr Ser Thr His Val Ile Thr
1               5                   10                  15

<210> SEQ ID NO 13
<211> LENGTH: 16
<212> TYPE: PRT
<213> ORGANISM: Clostridium difficile

<400> SEQUENCE: 13

Met Gly Ile Asp Tyr Gln Cys Gly Thr Gly His Gly Ile Gly Phe Val
1               5                   10                  15

<210> SEQ ID NO 14
<211> LENGTH: 5
<212> TYPE: PRT
<213> ORGANISM: Clostridium difficile

<400> SEQUENCE: 14

Lys Lys Gly Ile Lys
1               5

<210> SEQ ID NO 15
<211> LENGTH: 9
<212> TYPE: PRT
<213> ORGANISM: Clostridium difficile

<400> SEQUENCE: 15

Lys Gly Thr Ser Thr His Val Ile Thr
1               5

<210> SEQ ID NO 16
<211> LENGTH: 16
<212> TYPE: PRT
<213> ORGANISM: Clostridium difficile

<400> SEQUENCE: 16

Ala Thr Gly Lys Lys Gly Ser Glu Thr Pro Thr Gly Lys Thr Lys Val
1               5                   10                  15

<210> SEQ ID NO 17
<211> LENGTH: 16
<212> TYPE: PRT
<213> ORGANISM: Clostridium difficile

<400> SEQUENCE: 17

Thr Gly Trp Lys Thr Glu Asn Gly Lys Lys Tyr Tyr Val Lys Ser Asp
```

<210> SEQ ID NO 18
<211> LENGTH: 16
<212> TYPE: PRT
<213> ORGANISM: Clostridium difficile

<400> SEQUENCE: 18

Asn Lys Lys Tyr Tyr Leu Gly Thr Asp Gly Ala Arg Val Ser Gly Trp
1               5                   10                  15

<210> SEQ ID NO 19
<211> LENGTH: 16
<212> TYPE: PRT
<213> ORGANISM: Clostridium difficile

<400> SEQUENCE: 19

Phe Asp Thr Ala Lys Lys Ile Ser Ser Val Gly Asn Trp Asn Ala Asp
1               5                   10                  15

<210> SEQ ID NO 20
<211> LENGTH: 16
<212> TYPE: PRT
<213> ORGANISM: Clostridium difficile

<400> SEQUENCE: 20

Phe Ile Ser Gly Phe Asn Gly Ser Ala Gly Thr Val Ile Val Thr Lys
1               5                   10                  15

<210> SEQ ID NO 21
<211> LENGTH: 17
<212> TYPE: PRT
<213> ORGANISM: Clostridium difficile

<400> SEQUENCE: 21

Arg Glu Gly Ala Thr Leu Ala Glu Lys Lys Leu Ser Lys Lys Gly Ile
1               5                   10                  15
Lys

<210> SEQ ID NO 22
<211> LENGTH: 16
<212> TYPE: PRT
<213> ORGANISM: Clostridium difficile

<400> SEQUENCE: 22

Lys Lys Gly Ile Lys Ile Glu Tyr Gln Tyr Asp Leu Ile Asp Gly Ile
1               5                   10                  15

<210> SEQ ID NO 23
<211> LENGTH: 16
<212> TYPE: PRT
<213> ORGANISM: Clostridium difficile

<400> SEQUENCE: 23

Val Asn Lys Ile Lys Asn Arg Pro Tyr Tyr Lys Gly Asn Ile Pro Gly
1               5                   10                  15

```
<210> SEQ ID NO 24
<211> LENGTH: 16
<212> TYPE: PRT
<213> ORGANISM: Clostridium difficile

<400> SEQUENCE: 24

Ser Arg Lys Asn Thr Leu Gly Tyr Phe Val Asn Asn Lys Leu Val Lys
1               5                   10                  15
```